(12) United States Patent
Kapusta et al.

(10) Patent No.: US 11,129,604 B2
(45) Date of Patent: Sep. 28, 2021

(54) SCLERAL DEPRESSION MECHANICAL ASSIST DEVICE

(71) Applicant: 11789473 CANADA INC. (KVW SURGICAL), Hampstead (CA)

(72) Inventors: Michael Alton Kapusta, Hampstead (CA); Natàlia Vilà Grané, Montréal (CA); Jean-Laurent Wilson, Kirkland (CA)

(73) Assignee: 11789473 CANADA INC. (KVW SURGICAL), Hampstead (CA)

( * ) Notice: Subject to any disclaimer, the term of this patent is extended or adjusted under 35 U.S.C. 154(b) by 0 days.

(21) Appl. No.: 16/973,015

(22) PCT Filed: Jun. 10, 2019

(86) PCT No.: PCT/IB2019/000799
§ 371 (c)(1),
(2) Date: Dec. 7, 2020

(87) PCT Pub. No.: WO2020/008260
PCT Pub. Date: Jan. 9, 2020

(65) Prior Publication Data
US 2021/0244400 A1    Aug. 12, 2021

(51) Int. Cl.
*A61B 17/02*      (2006.01)
(52) U.S. Cl.
CPC ...... *A61B 17/0231* (2013.01); *A61B 17/0293* (2013.01)
(58) Field of Classification Search
CPC .................. A61B 17/0231; A61B 17/0293

USPC ................................................. 600/233, 236
See application file for complete search history.

(56) References Cited

U.S. PATENT DOCUMENTS

| 6,440,065 | B1 | 8/2002 | Hered | |
|---|---|---|---|---|
| 9,289,199 | B1 | 3/2016 | Sami et al. | |
| 2003/0109885 | A1* | 6/2003 | Tano | A61F 9/007 606/107 |
| 2004/0204727 | A1 | 10/2004 | Olsen et al. | |
| 2008/0081952 | A1* | 4/2008 | Josephberg | A61B 17/0231 600/236 |
| 2008/0091224 | A1* | 4/2008 | Griffis, III | A61B 17/30 606/166 |
| 2012/0071726 | A1* | 3/2012 | Beck | A61B 1/32 600/214 |
| 2013/0103145 | A1 | 4/2013 | John et al. | |
| 2015/0359529 | A1 | 12/2015 | Ganiban et al. | |
| 2017/0049320 | A1* | 2/2017 | Nishizaki | A61B 3/117 |

(Continued)

*Primary Examiner* — Eduardo C Robert
*Assistant Examiner* — David C Comstock
(74) *Attorney, Agent, or Firm* — Patent Technologies, LLC; Robert D. Gunderman, Jr.

(57) ABSTRACT

A device for mechanically assisting with scleral depression is disclosed. A top ring and a bottom ring are rotationally engaged where the bottom ring is capable of attachment to an eyelid speculum, and is thus fixed while in use. A variable vertical displacement apparatus is attached to the top ring. A rod and depressing member are engaged with the variable vertical displacement apparatus such that the depressing member is capable of both vertical and horizontal travel around the periphery of a patient's eye, allowing a surgeon to depress the sclera of a patient's eye while at the same time performing a surgical procedure.

21 Claims, 37 Drawing Sheets

(56) References Cited

U.S. PATENT DOCUMENTS

2017/0079528 A1 3/2017 Farley et al.
2020/0187930 A1* 6/2020 Zacharia ................ A61B 90/30

* cited by examiner

SCLERAL DEPRESSION MECHANICAL ASSIST DEVICE

CROSS REFERENCE TO RELATED PATENT APPLICATIONS

This application claims priority to Canadian Patent Application Serial No. 3,007,718 filed Jun. 11, 2018 entitled "Scleral Depression Mechanical Assistant Device" by Dr. Michael Alton Kapusta et al., and to International Application Number PCT/IB2019/000799 filed Jun. 10, 2019 entitled "Scleral Depression Mechanical Assist Device", the entire disclosures of which are incorporated herein by reference in their entirety.

TECHNICAL FIELD

The present invention relates generally to eye surgery and examination instruments, and more particularly to a device to assist with scleral depression of the eye.

BACKGROUND ART

Pars plana vitrectomy (PPV) is a surgical procedure that involves removal of vitreous gel from the eye. This procedure is indicated in several retinal and eye conditions, such as retinal detachment (rhegmatogenous or tractional), macular pathology (vitreoretinal interface, macular edema), vascular diseases and complications, diabetic retinopathy, inflammatory and infectious diseases (uveitis, endophthalmitis), complications of cataract surgery (retained lens fragments, nucleus loss dislocated intraocular lens), trauma (penetrating injuries, blunt trauma, intraocular foreign bodies), new therapies (cellular and genetic intraocular treatments), retinal prosthesis, and floaters.

In Pars plana vitrectomy (PPV), the surgeon will make three small incisions in the eye to create openings (sclerotomies) for various instruments to be inserted during the procedure. These incisions are placed in the pars plana of the eye, located just behind the iris but in front of the retina. The instruments that pass through these incisions include as standard setup a light pipe, an infusion line, and a vitrector. The light pipe serves as a light source for use within the eye; the infusion line is used to maintain eye pressure during surgery with balanced saline solution; and the vitrector is a cutting and aspirating device that removes vitreous gel within the eye in a controlled fashion, to avoid retinal traction or damage.

During retina surgery, visualization is crucial. Pars plana vitrectomy surgery poses a number of unique challenges. Many of the tissues involved are nearly transparent, the globe is relatively small in size, and specialized optical systems are often required to see within the eye during surgery. Specialized lens systems are used to visualize the back of the eye and view the retina during surgery or examination.

During pars plana vitrectomy, in order to completely remove the vitreous-gel, the surgeon must be able to access and visualize the vitreous inside of the eye. The surgical view during this procedure is through a dilated pupil, which offers a view limited by the size of the dilated pupil opening. To optimize the view of the anterior vitreous, a surgical assistant typically employs a manual surgical instrument called scleral depressor that is used to push the exterior sidewalls of the eye inward to create a temporary indentation inside the eye. This scleral depression technique allows the surgeon to visualize the anterior vitreous and facilitate completion of a 360 degrees vitreous shaving. While this scleral depression technique allows efficient removal of peripheral and anterior vitreous, it is not without limitations and shortcomings. The ability to perform a complete PPV is often dependent upon the availability of a technically proficient assistant. In the absence of such personnel, surgical complications associated with an incomplete vitreous removal can occur and surgical outcomes may be compromised. The lack of an assistant during vitrectomy surgery is very common in a non-academic setting, and is also frequent in academic institutions. In addition, the surgical assistant along with the surgeon are both working in close quarters on the eye, and can interfere with each other during the procedure. For example, 360 degree movement of the scleral depressor around the eye is often required. This movement requires space, and is impeded by other surgical steps performed by the surgeon, or even anatomical parts of the patient such as the patient's nose.

What is therefore needed is a device that allows a surgeon to depress the sclera around the entire 360 degree perimeter of the eye while performing other surgical tasks.

DISCLOSURE OF THE INVENTION

In accordance with the present invention, there is provided a device for mechanically assisting with scleral depression, the device comprising a ring for attachment to a device such as an eyelid speculum, a variable vertical displacement apparatus rotationally coupled to the ring, a rod having an adjustment end and a surgical end, and a depressing member attached to the surgical end of the rod, where the adjustment end of the rod is adjustably coupled to the variable vertical displacement apparatus.

The foregoing has been provided by way of introduction, and is not intended to limit the scope of the invention as described by this specification, claims and the attached drawings.

BRIEF DESCRIPTION OF THE DRAWINGS

The invention will be described by reference to the following drawings, in which like numerals refer to like elements, and in which.

Figure 1:
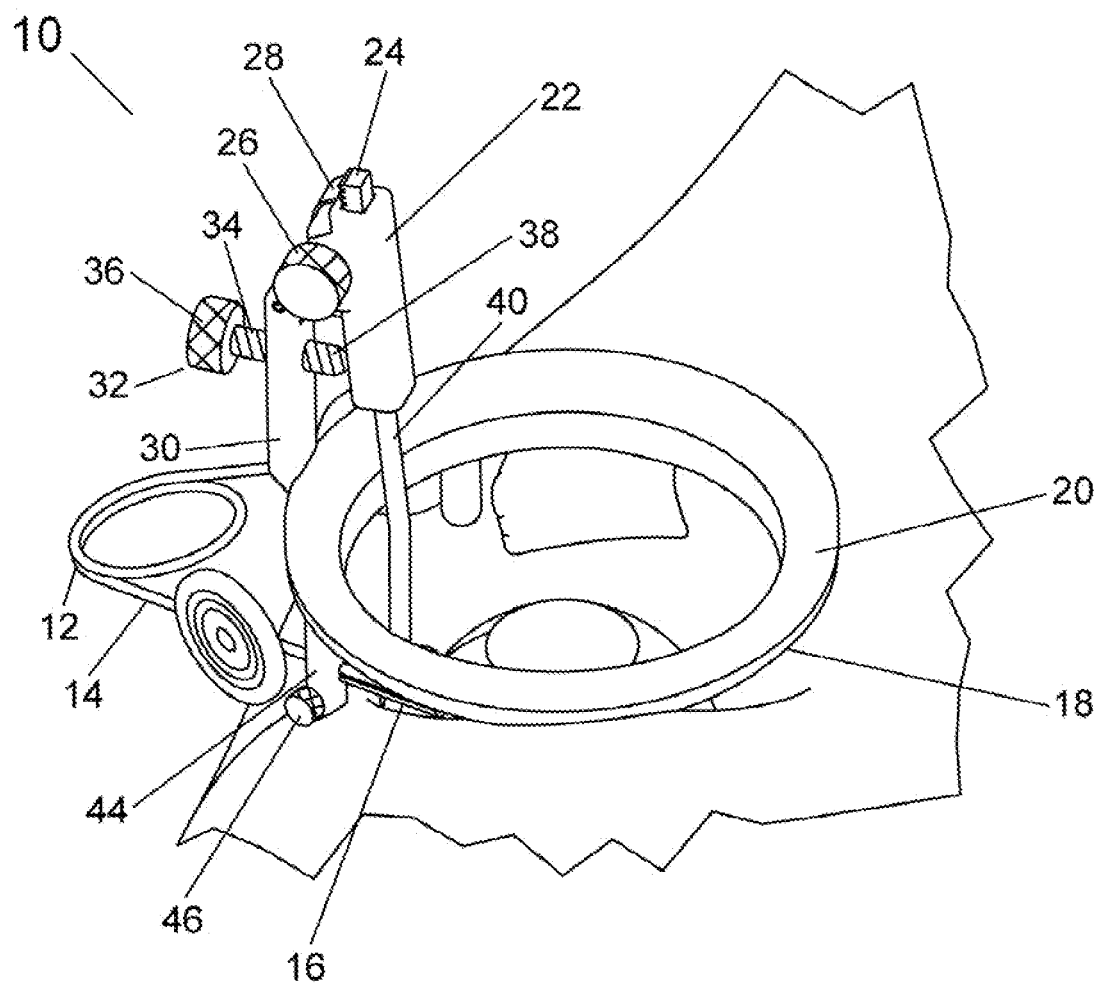
FIG. 1 is a perspective view of the scleral depression mechanical assist device in use.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, claims and drawings attached hereto.

BEST MODE FOR CARRYING OUT THE INVENTION

A scleral depression mechanical assist device is disclosed. Several embodiments are described herein by way of this detailed disclosure and accompanying drawings. The scleral depression mechanical assist device attaches to a device such as a speculum or similar surgical instrument or the like. An eyelid speculum, for example, engages with the eyelids of a patient to retain the eyelids in a separated position during surgery or examination and makes for a convenient and practical attachment for the scleral depression mechanical assist device. Additionally and importantly, the ring-like structure of the device allows for the use of numerous types of lenses and related surgical and diagnostic instruments with the device, providing for unobstructed and efficient surgical and diagnostic procedures that have heretofore not been possible.

As will be described and depicted herein, additional accessories may be utilized with the scleral depression mechanical assist device to provide increased stability, ease of use, convenience, or the like.

Turning to a first embodiment of the present invention depicted by way of FIGS. 1-6, a perspective view of the scleral depression mechanical assist device can be seen attached to an eyelid speculum which is in turn retaining a patient's eyelids in a separated position. In some embodiments of the present invention the eyelid speculum is incorporated with, or otherwise attached to, affixed, or formed with the scleral mechanical assist device. Further embodiments may employ or engage with other devices.

The scleral depression mechanical assist device is manufactured using surgical grade materials such as stainless steel, titanium, surgical grade plastics, or the like. The scleral depression mechanical assist device is manufactured by way of machining, stamping, casting, injection molding, 3D printing, or any suitable manufacturing method capable of producing the device as described herein.

The scleral depression mechanical assist device has a ring-like structure. The device comprises a ring for attachment to a device such as an eyelid speculum, a variable vertical displacement apparatus rotationally coupled to the ring, a rod having an adjustment end and a surgical end, and a depressing member attached to the surgical end of the rod, where the adjustment end of the rod is adjustably coupled to the variable vertical displacement apparatus.

As described herein by way of example and not limitation, the device in one embodiment comprises a top ring rotationally disposed with a bottom ring, a locking member attached to the bottom ring for attachment to an eyelid speculum, an upright frame member attached to the top ring, a rod having an adjustment end and a surgical end, a variable vertical displacement apparatus mechanically coupled to both the upright frame member and the rod, the variable vertical displacement apparatus configured to provide vertical displacement to the rod, a depressing member attached to the surgical end of the rod, and an adjusting member for providing horizontal displacement to the rod and depressing member. The various embodiments of the present invention will be described herein by way of the attached drawings and detailed description provided.

Turning first to FIG. 1, the scleral depression mechanical assist device 10 can be seen coupled with a very basic eyelid speculum 12 in use with a patient. The disclosure provided herein will depict additional, and perhaps more advanced or different, eyelid speculums, but the basic eyelid speculum 12 depicted in FIG. 1 and related figures is described first for ease of description. The basic speculum 12 is comprised of a wire like member 14 with a pair of retaining members 16 designed to engage with the eyelids of a patient in order to retain the patient's eyelids in a separated position.

A top ring 20 and a bottom ring 18 can be seen rotationally engaged or disposed with each other. The rotational surfaces of each ring may be grooved, channeled, machined, or otherwise contain locking or mating surfaces. The rotational surfaces may also have features or finishes that provide friction reducing engagement, or in some embodiments of the present invention, a specific or adjustable coefficient of friction that may be suitable for various surgical or diagnostic procedures, or may be optimal for a given surgeon or medical practitioner. The bottom ring 18 has at least one locking member 44 attached to a lower surface such that the sclera depression mechanical assist device can be attached to an eyelid speculum such as 12. The locking member 44 has retention hardware such as a locking screw 46 for frictional or mechanical retention of the eyelid speculum 12. The locking member 44 protrudes or otherwise extends toward the eyelid speculum 12, and may be of any convenient geometry, such as cylindrical, square, octagonal, rectangular, or the like.

A rod 40 can also be seen protruding downward from a variable vertical displacement apparatus. The rod 40 can be adjusted vertically by way of a gear and knob arrangement, and may also be displaced horizontally by way of an adjusting member 32 with an adjusting end 38. The adjusting member 32 may be, for example, a screw, a bolt, a threaded fixture, or the like, and serves to apply horizontal force and subsequent displacement to the rod 40. To facilitate movement of the rod 40, a hinge or pin arrangement is provided, as will be further described herein. The hinge or pin arrangement may contain additional mechanical features to allow further degrees of movement and adjustability. Further, the rod 40 may be straight, or may, in some embodiments, contain a curve or angle to allow for more specific placement of the depressing member 42, clearance of the ring structure, or the like.

Figure 2:
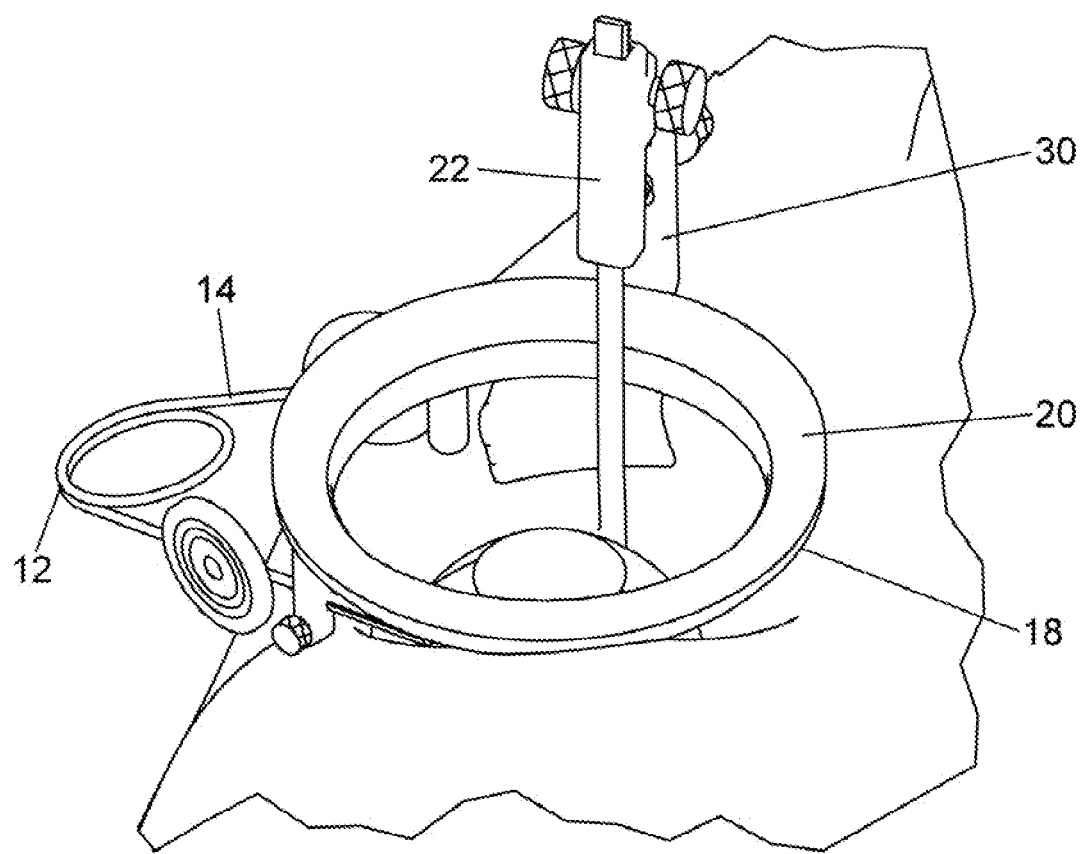
FIG. 2 is a further perspective view of the device of FIG. 1 being circumferentially operated 90 degrees from the view shown in FIG. 1.

Turning now to FIG. 2, the scleral depression mechanical assist device 10 can be seen with the top ring 20 and related mechanical structures rotated 90 degrees from the position depicted in FIG. 1. An upright frame member 30 can be seen attached to the top ring 20 with a housing 22 pivotally attached to the upright frame member 30. The housing 22 contains a vertical displacement arrangement, which may hereinafter also be referred to as a variable vertical displacement apparatus 22, which is in turn connected to the rod 40. The vertical displacement arrangement may, in one example, be a rack gear 24 with an engaging gear (not seen in FIG. 2) where the engaging gear is coupled to a knob such as a first knob 26 and a second knob 28. With this arrangement, tactile movement of either knob provides rotational movement of the engaging gear and subsequent linear displacement of the rod 40. The rack gear 24 or related vertical member may also employ one or more travel stops to halt the linear movement of the rod 40 and related depressing member 42. The travel stop in some embodiments may be adjustable or otherwise variable or removable. It should be noted that a friction device or other retention device may be employed to reduce or eliminate unwanted movement of the rod 40 and attached depressing member 42. A friction creating device such as a frictional pad, gear, disc, rod, or the like may be used to hold the rod 40 in place. A lever, actuator, cam, or similar structure may also be employed to engage with the rack gear 24, rod 40 or related engaging gear or similar structure to prevent unwanted movement of the rod 40 and attached depressing member 42. A depressing member 42 will be later seen in FIGS. 3-5 that contacts the eye to generate a concave shape on the side of the eye to expose vitreous and allow a complete visualization of the anterior vitreous. The horizontal movement of the rod 40 by way of the pivot and adjusting member 32 controls the depth of the concave shape so formed, and the rotation of the top ring 20 with respect to the bottom ring 18 allows such concave depression to be made around a periphery of the eye, at the control and direction of the surgeon or medical practitioner performing a given procedure. The adjusting member 32 can be seen with a shaft 34 and a knob 36. In one example, the adjusting member 32 has a screw-thread shaft. Other examples may include frictional or locking engagement of the adjusting member with respect to the upright frame member 30. In some embodiments of the present invention, an adjusting end 38 that may have a pointed or tapered tip may be employed to provide positive and precise adjustment of the horizontal displacement of the rod 40.

In some embodiments of the present invention, the depressing member 42 may contain a light source or light guide. Such an arrangement may comprise, for example, a fiber optic element, a light emitting diode, or a fluorescent material. A biocompatible or surgical grade plastic may also be employed that may, in some embodiments, have optical characteristics, or may include fluorescent material that may be optically charged. In the example of an electrically powered light source, an appropriate source of electrical power is provided that may include batteries, external wires with a power source, or the like. One suitable light source is an existing fiber optic surgical illumination system where a fiber optic element is inserted into or otherwise in optical communication with the depressing member 42. While the light may be in the visible spectrum, other wavelengths may be employed that are detectable by instrumentation to provide additional diagnostic or analytical functionality.

Figure 3:
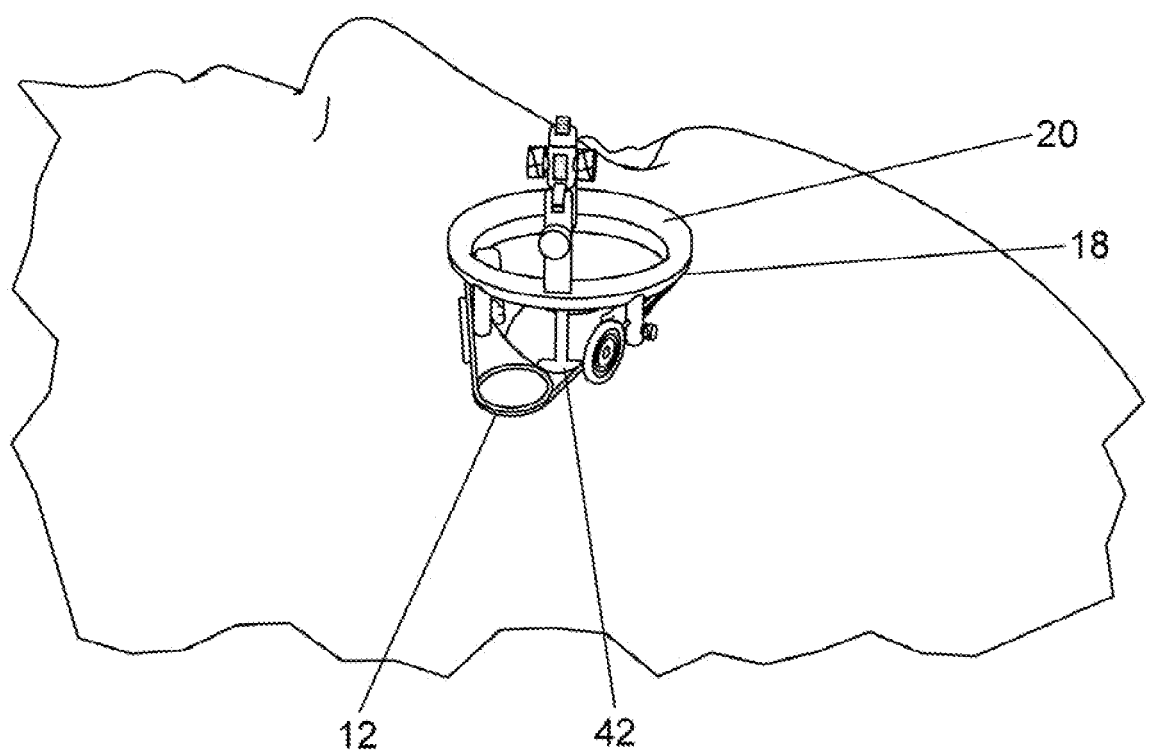
FIG. 3 is a side perspective view of the device of FIG. 1 in use.

FIG. 3 depicts a further perspective view of the scleral depression mechanical assist device 10 showing the depressing member 42 affixed to or otherwise formed with the rod 40. The depressing member 42, in one embodiment, may be cylindrical or otherwise rounded, and may also have convex ends. In one embodiment, the depressing member 42 is attached to the rod 40 in a T like arrangement with the rod 40 connecting with a center point of the cylindrical form of the depressing member 42. The depressing member 42 may also be spherical or have rounded or convex ends. The top ring 20 and the bottom ring 18 can also be seen with the variable vertical displacement apparatus housing 22 affixed to the top ring 20. The ring-like arrangement of the device of the present invention affords the surgeon with the ability to place a lens within the ring-like structure of the device and rotate the scleral depressor apparatus around the lens without mechanical interference or obstruction.

Figure 4:
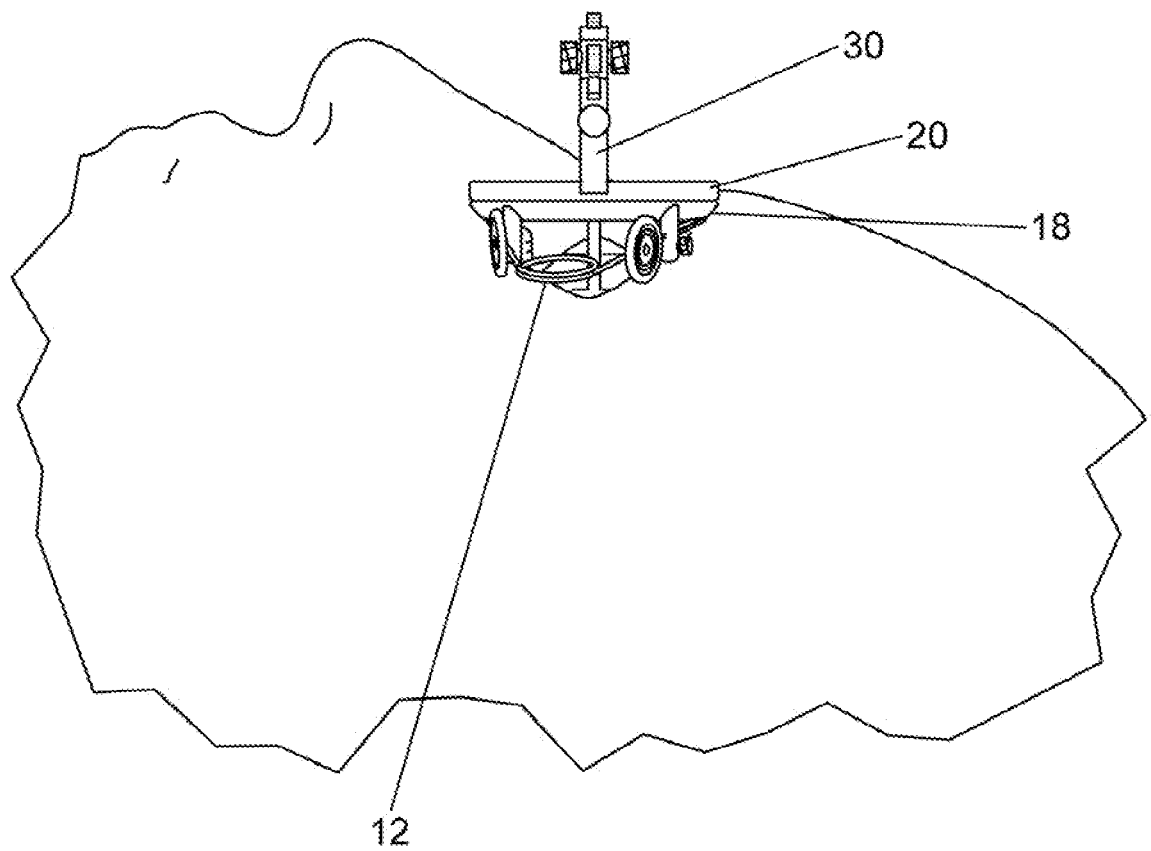
FIG. 4 is a side view of the device of FIG. 1 in use.
Figure 5:
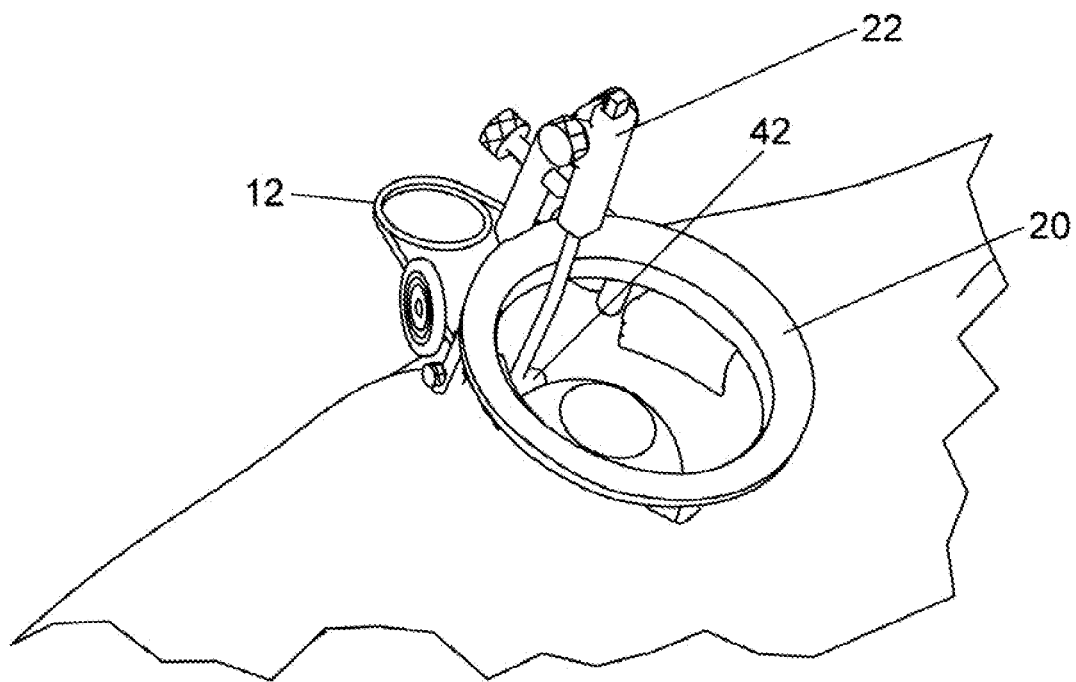
FIG. 5 is a top perspective view of the device of FIG. 1 in use.
Figure 6:
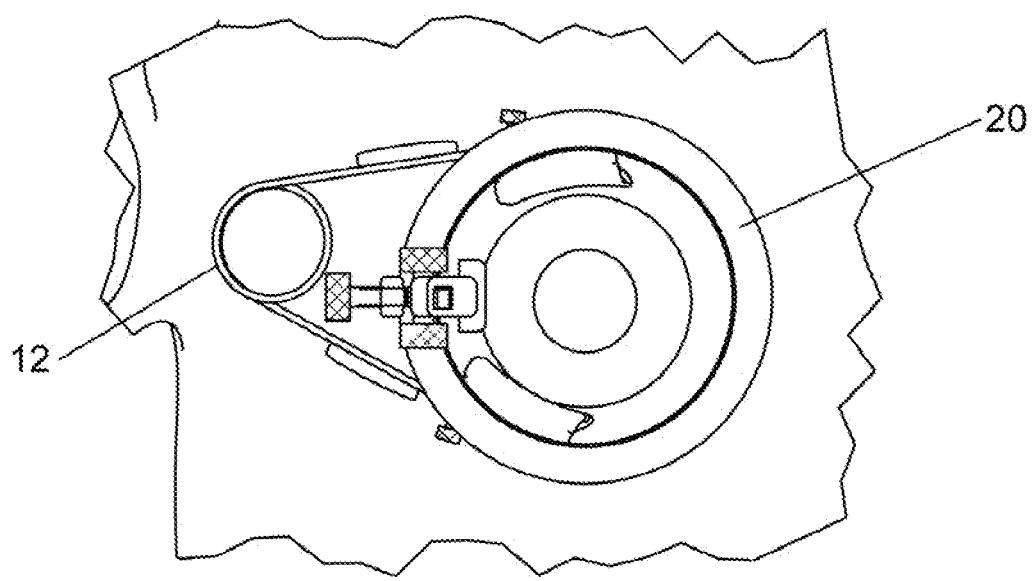
FIG. 6 is a top plan view of the device of FIG. 1.

FIG. 4 provides a side view of the scleral depression mechanical assist device further showing the vertically displaceable rod 40 and related depressing member 42. FIG. 5 shows another perspective view of the scleral depression mechanical assist device in use. FIG. 6 depicts a top plan view of the scleral depression mechanical assist device in use where the rotation about the periphery of the eye is evident and the positioning of the eyelid speculum can be seen.

Turning now to FIGS. 7-13, the scleral depression mechanical assist device can be seen with support struts affixed or otherwise attached. The support struts are attached to a portion of the scleral depression mechanical assist device, and in one embodiment are attached or joined to the bottom ring 18. A nose support strut can be seen in FIG. 7 with a curve or profile that conforms to a patient's nose. The curve or profile may, in some embodiments, be adjustable to better conform to a patient. A peripheral support strut 73 can also be seen that has a profile or curve that conforms to the side of a patient's head, and also, in some embodiments, may be adjustable. The support struts are preferably, but not necessarily, flat or of a planar geometry to better rest on the patient without rotation or movement. The peripheral support strut 73 may also be used as a handle, stabilizer, or means of adjustment of the scleral depression mechanical assist device.

Figure 7:
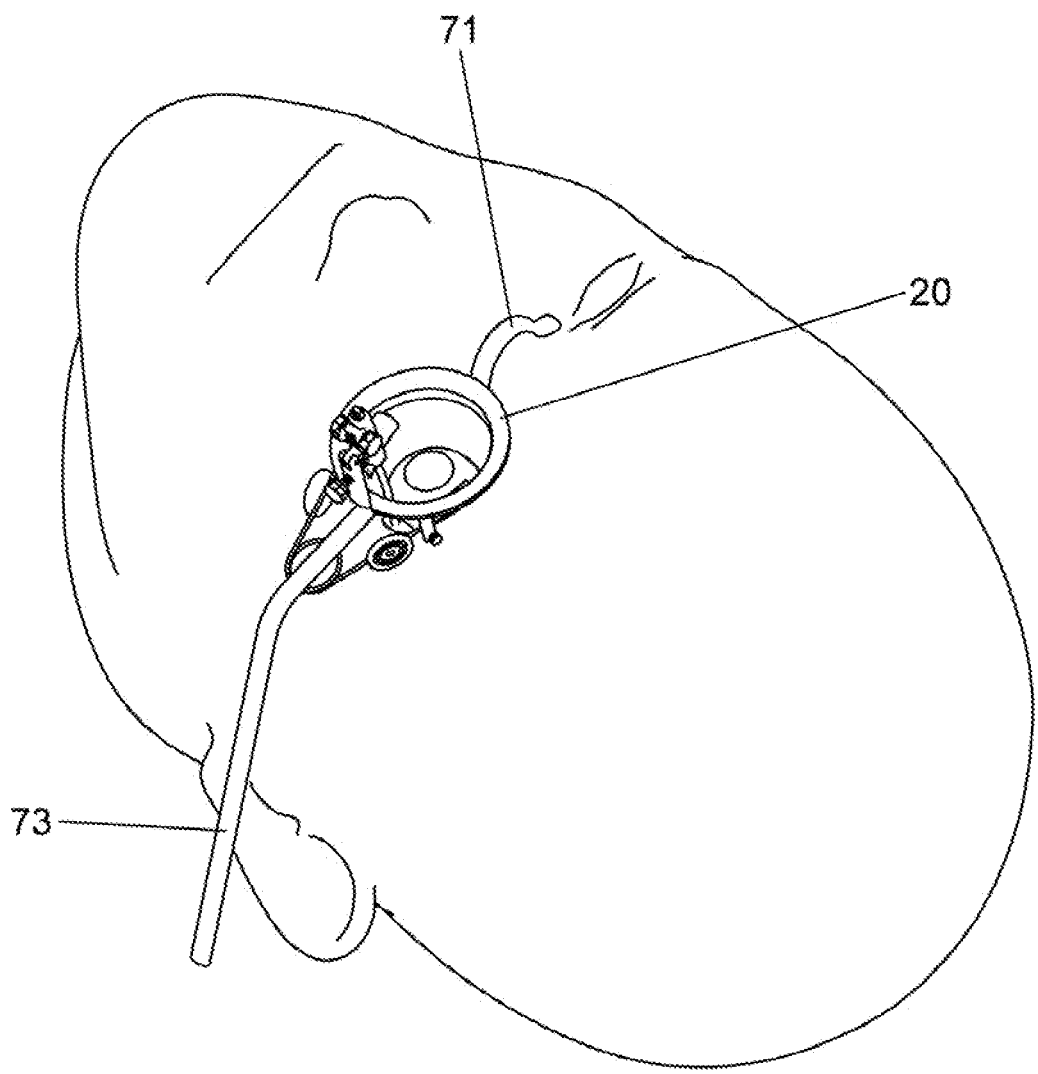
FIG. 7 is a perspective view of the device of FIG. 1 in use with support struts.
Figure 8:
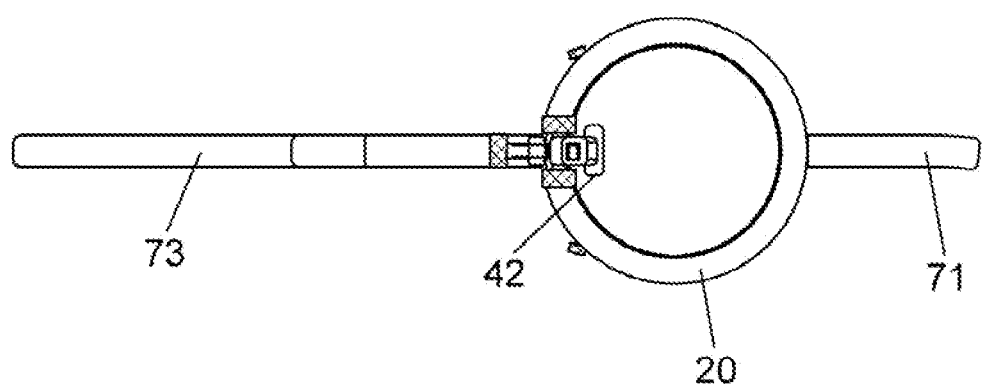
FIG. 8 is a top plan view of the device of FIG. 7.

FIG. 8 is a top plan view of the device of FIG. 7 where the orientation of the support struts in relation to the scleral depression mechanical assist device can be seen. The top ring 20 can be seen, and it is evident from FIG. 8 that a lens or other surgical or diagnostic devices may be placed within the ring-like form of the present invention.

Figure 9:
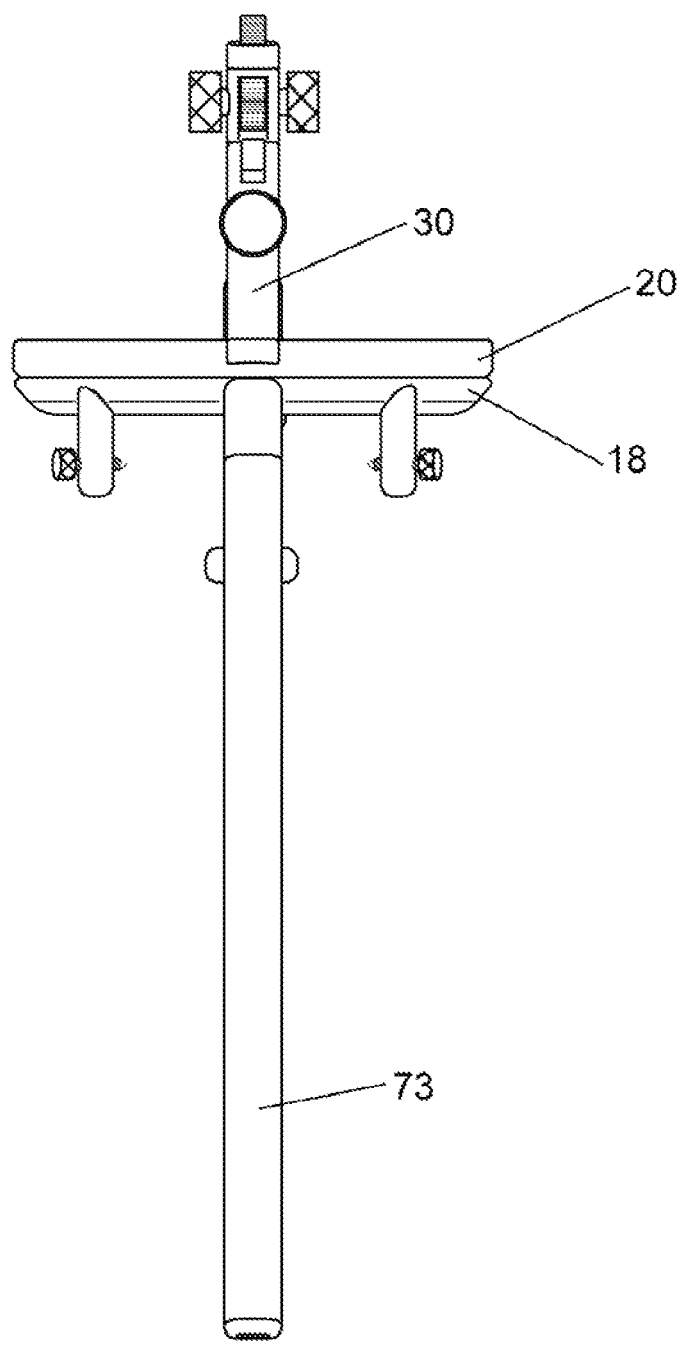
FIG. 9 is a side plan view of the device of FIG. 7.
Figure 10:
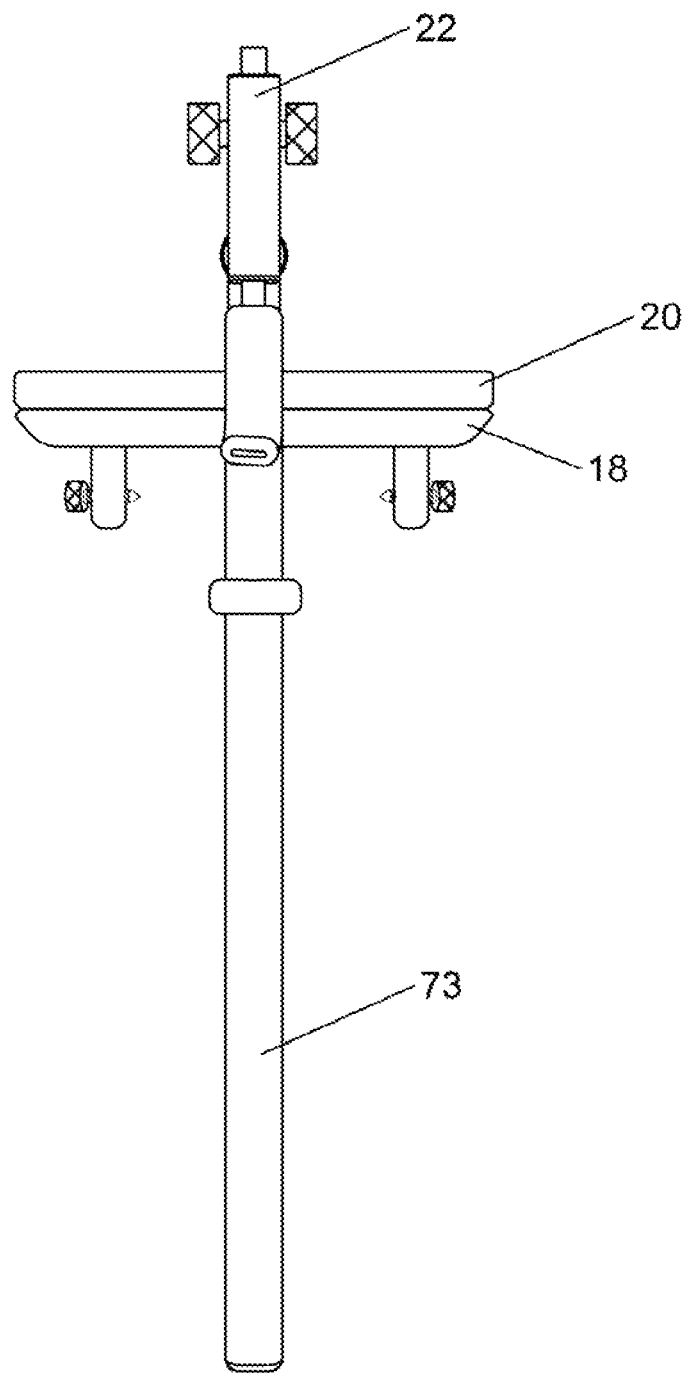
FIG. 10 is an alternate side plan view of the device of FIG. 7.

FIG. 9 is a side plan view of the device of FIG. 7 and FIG. 10 is an alternate side plan view of the device of FIG. 7 where the profile of the support struts can be seen. It is evident from this disclosure that other support strut geometries and configurations may also be possible and useful with the device of the present invention.

Figure 11:
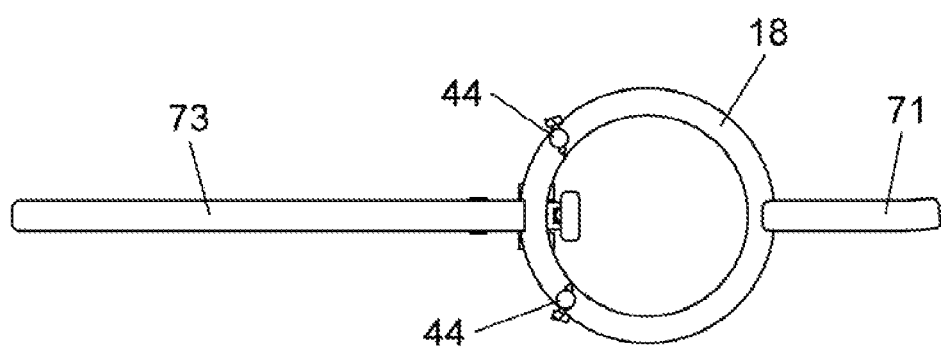
FIG. 11 is a bottom plan view of the device of FIG. 7.

FIG. 11 is a bottom plan view of the device of FIG. 7 where one example of locking members 44 can be seen for attachment to an eyelid speculum.

Figure 12:
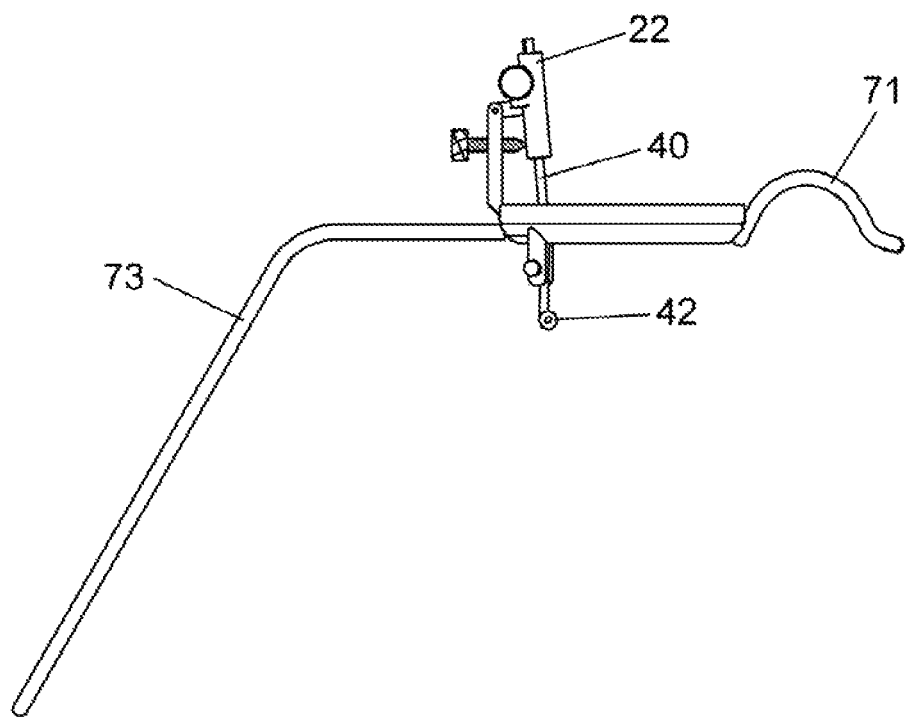
FIG. 12 is a rotated side plan view of the device of FIG. 7.

FIG. 12 is a rotated side plan view of the device of FIG. 7 where the profile of the nose support strut 71 can be clearly seen along with the peripheral support strut 73. The depressing member 42 can be seen protruding downwardly from the variable vertical displacement apparatus 22 and related top and bottom ring.

Figure 13:
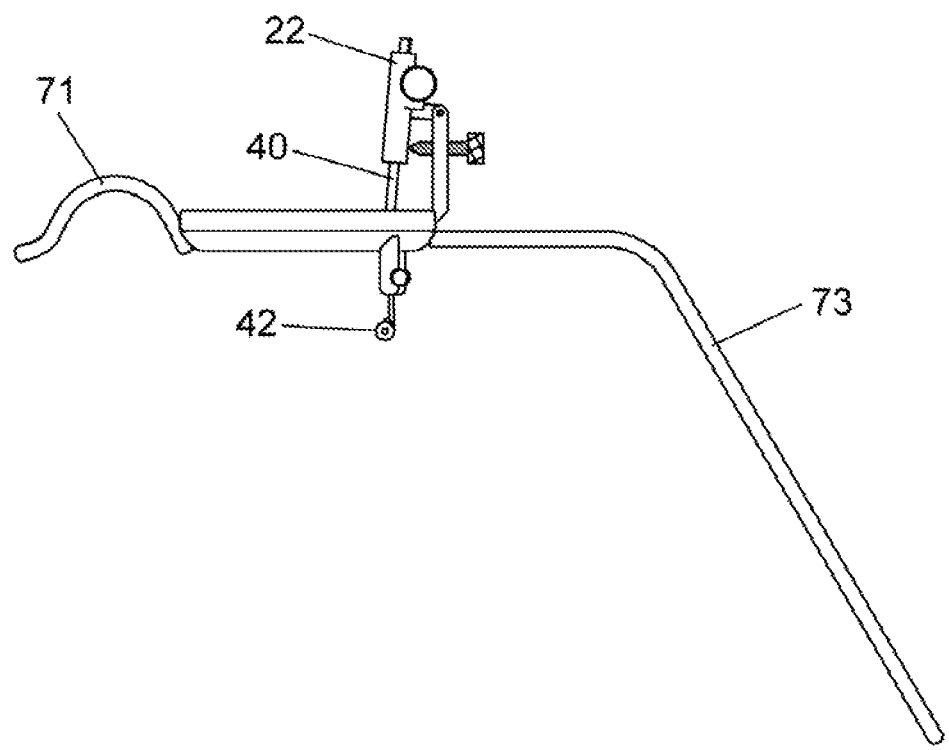
FIG. 13 is an alternate rotated side plan view of the device of FIG. 7.

FIG. 13 is an alternate rotated side plan view of the device of FIG. 7, and is similar to the view depicted in FIG. 12.

Figure 14:
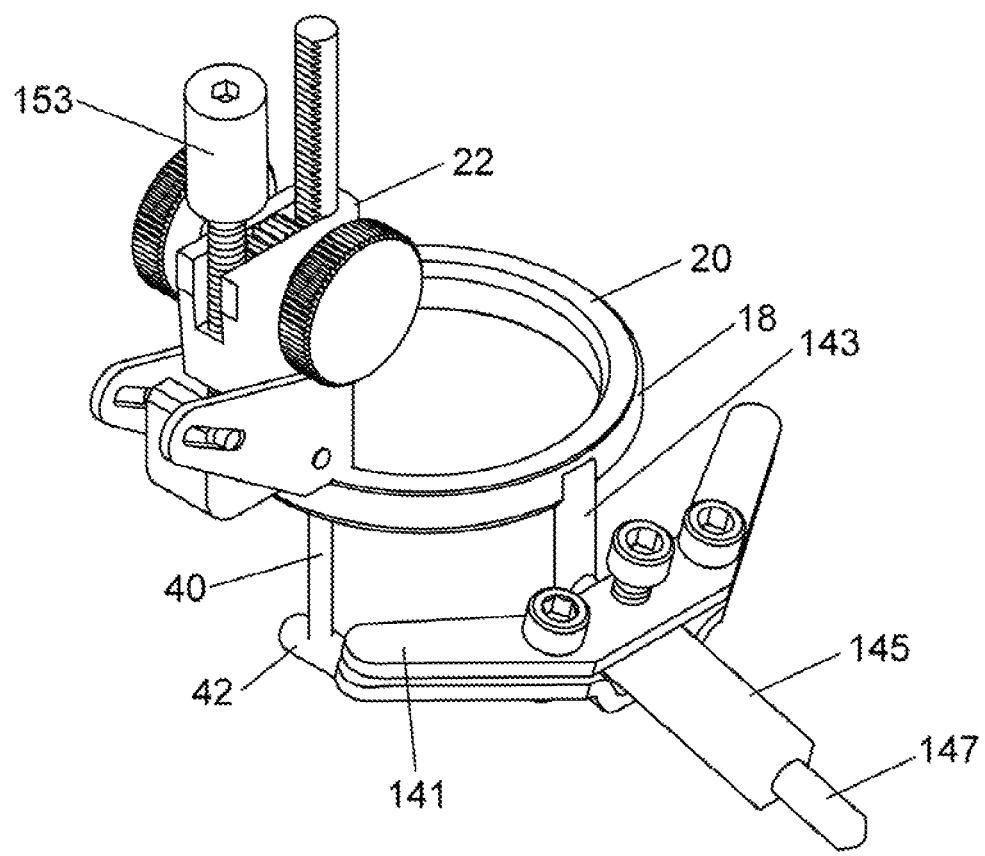
FIG. 14 is a perspective view of an alternate embodiment of the scleral depression mechanical assist device.
Figure 15:
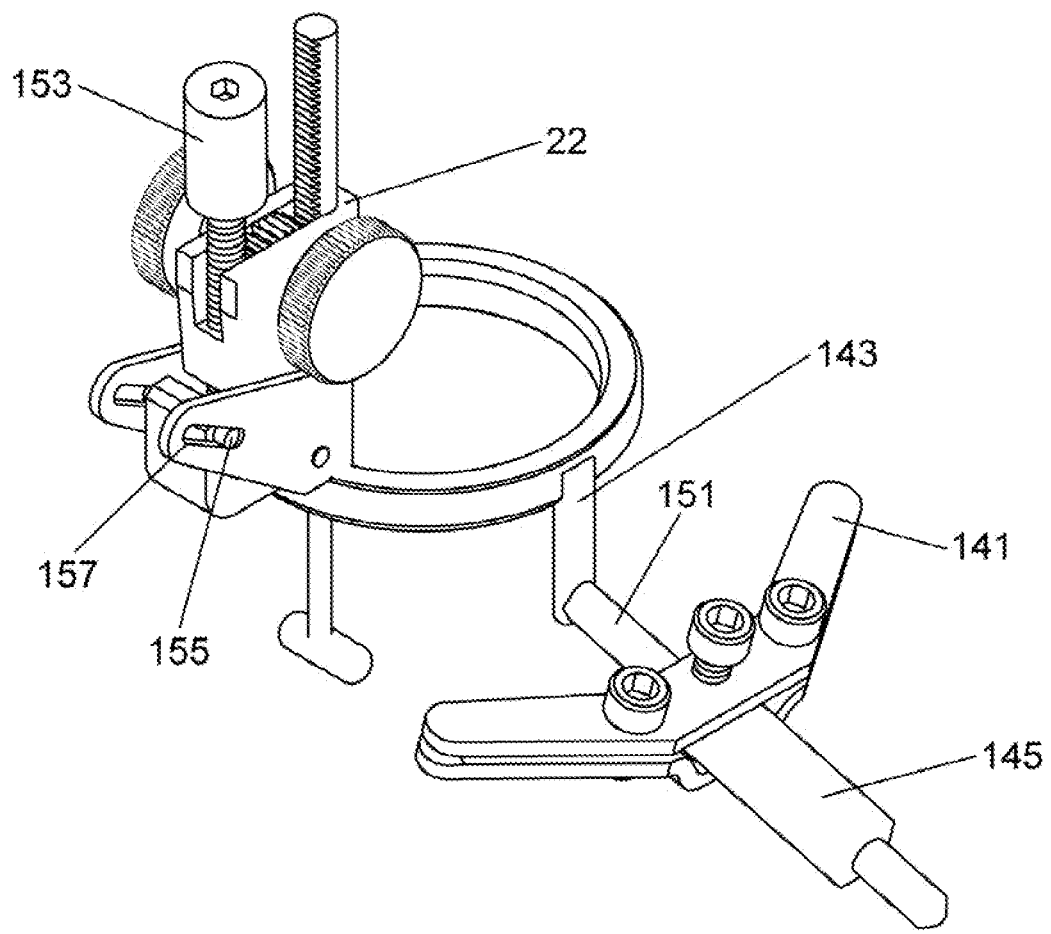
FIG. 15 is a perspective view of the device of FIG. 14 in an extended position.

Adjustability to suit a variety of patients and situations may also be provided by the device of the present invention. In addition, the present invention provides for varying configurations of eyelid speculum retainer components such as the eyelid speculum retainer 141 depicted in FIG. 14. Such a Y or V shaped speculum retainer 141 comprises two planar surfaces that are removably joined together with fasteners such as screws, bolts, clamps, pins, hinges, or the like. To provide adjustability of the scleral depression mechanical assist device in relation to the attached speculum, an attachment bridge 145 can be seen affixed or otherwise joined to a lower ring attachment 143 either directly or with an intermediary component, as seen in FIG. 15. The attachment bridge 145 may be square, rectangular, or cylindrical for example, and traverses through the speculum retainer 141 where it can be moved on a horizontal plane through the speculum retainer 141 and subsequently retained by way of a set screw, clamp, pin, or the like. The attachment bridge is perpendicularly or otherwise joined to the lower ring attachment 143, with the bottom ring attachment 143 in turn being joined to the bottom ring 18. In some embodiments, the angle of the bottom ring attachment 143 as joined to the bottom ring 18 is adjustable by way of a moveable joint, a set screw, a hinge, a pin and slot, or any coupling or joint that allows the angle to be varied and subsequently set or retained. Longitudinally attached to the attachment bridge 145 is a handle post 147 that may be cylindrical, square, octagonal, rectangular, or the like, and is configured for attachment to a handle, support strut, or other peripheral device or apparatus.

As seen in FIG. 15, the attachment bridge 145 is depicted in an extended position, revealing an extender 151 between the bottom ring attachment 143 and the attachment bridge 145. FIG. 15 also depicts a pin 155 that extends through a slotted flange 157 to provide adjustable horizontal displacement of the rod 40 and depressing member 42. The horizontal adjustment post 153 has threads that are mated threads provided with the housing of the variable vertical displacement apparatus 22 to apply adjustable displacement and subsequent horizontal travel of the rod 40 and depressing member 42. There may be two slotted flanges 157 with a pin through each slot, as depicted in FIG. 15. In some embodiments, the extender 151 moves in relation to the attachment bridge 145 and the attachment bridge 145 is joined or otherwise fixed to the speculum retainer 141.

Figure 16:
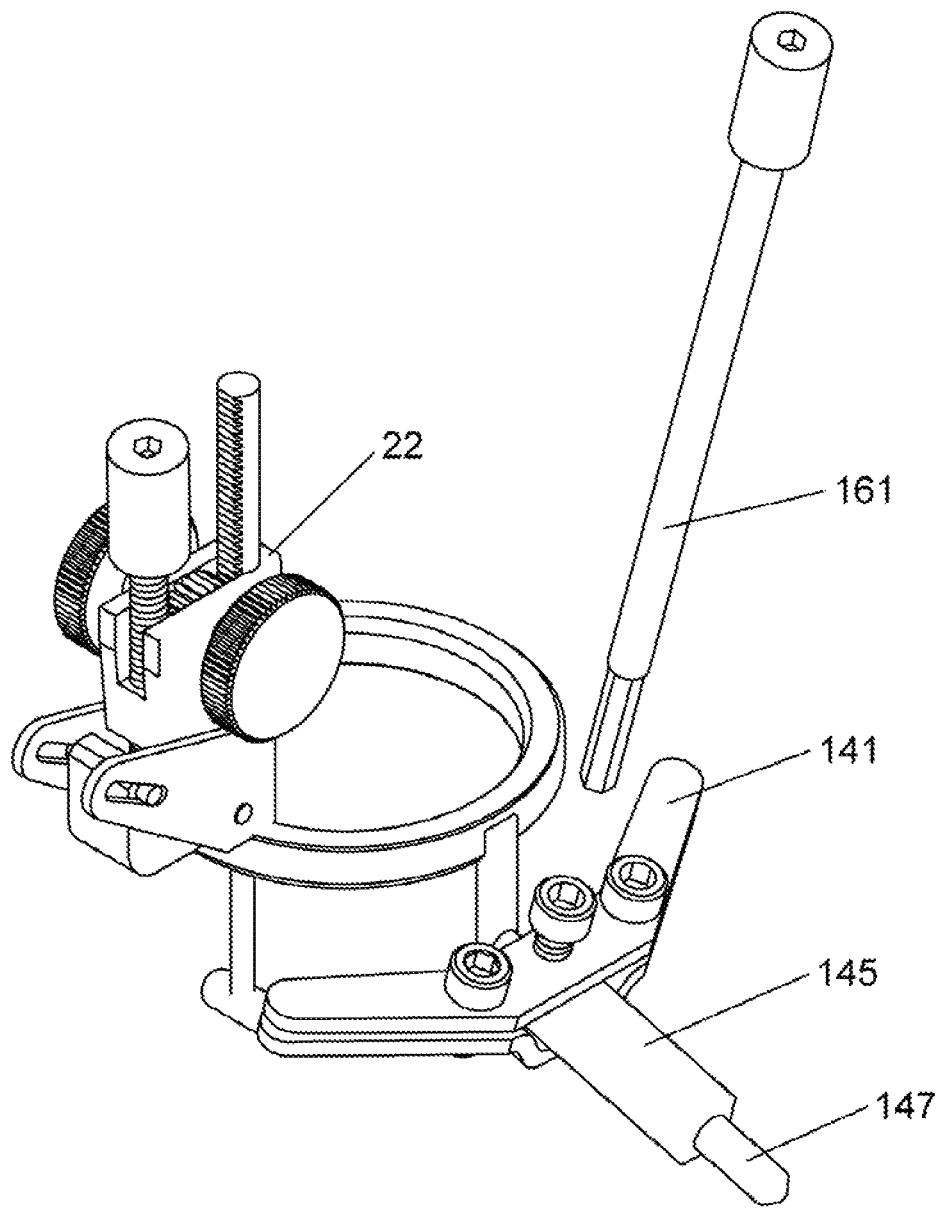
FIG. 16 is a perspective view of the device of FIG. 14 being locked in place.

FIG. 16 depicts the attachment bridge 145 locked in place by way of a set screw and hex driver 161. Other fasteners or fastening techniques may also be employed.

FIGS. 17-24 depict a further embodiment of the scleral depression mechanical assist device with a pivot 173 and pivot support 175 with a vertical adjusting member that engages with the pivot support 175, providing for a vertical knob with threads or similar engaging features that pushes against the pivot support 175, causing horizontal displacement of the rod and depressing member. The pivot 173 can be seen as a hinge style arrangement with a pin placed through corresponding holes in the pivot support 175 and corresponding variable vertical displacement apparatus. The pivot support 175 is attached to the top ring 20, and has a curved or otherwise angled shape. A handle 171 can be seen retained to the scleral depression mechanical assist device with a set screw.

Figure 17:
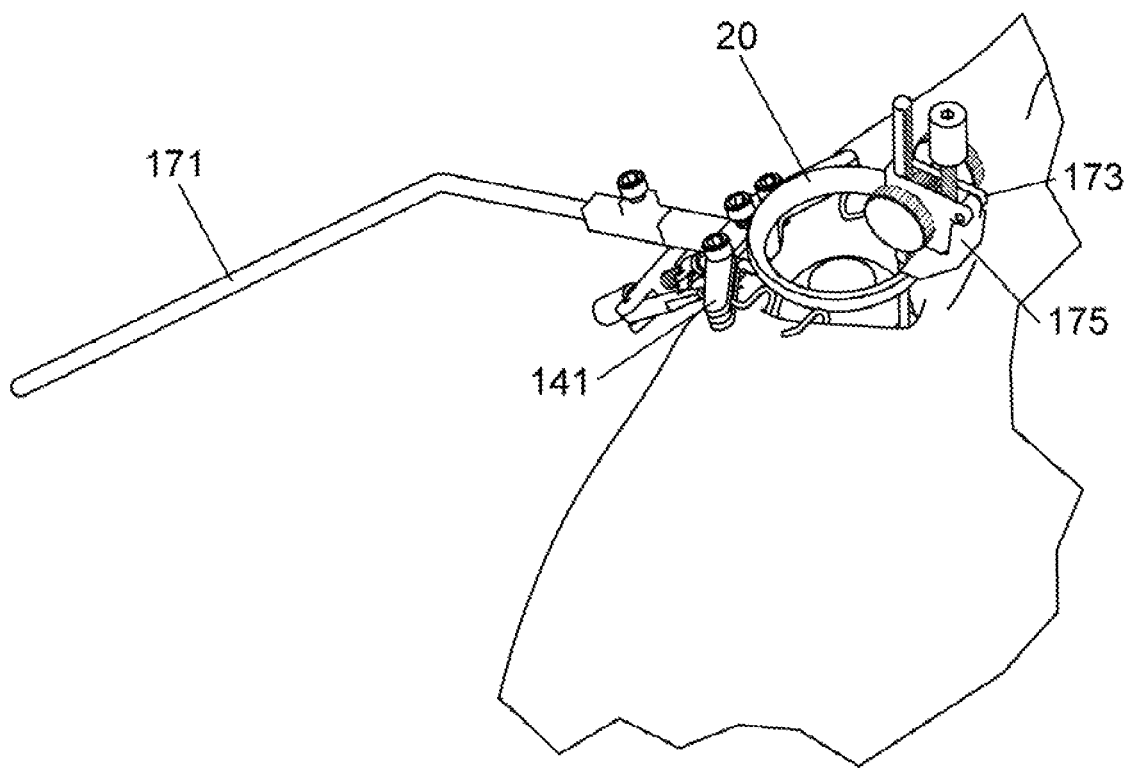
FIG. 17 is a perspective view of a further embodiment of the scleral depression mechanical assist device in use.
Figure 18:
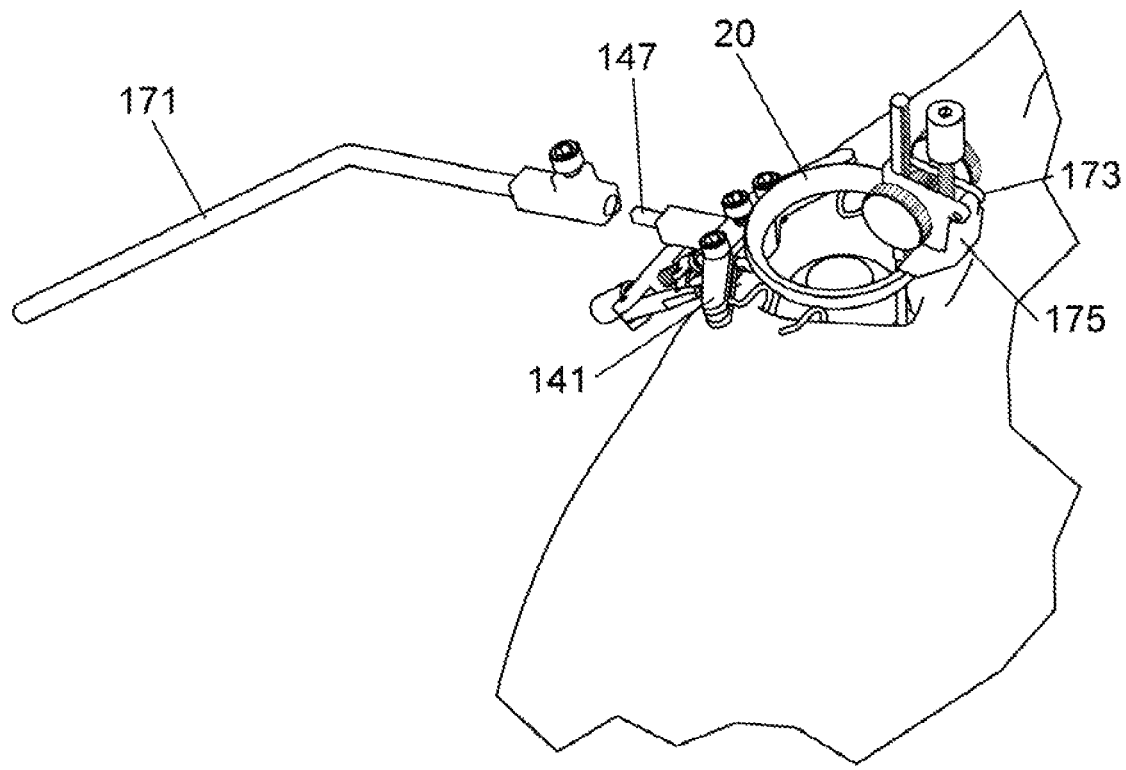
FIG. 18 is a perspective view of the device of FIG. 17 with the handle detached.

FIG. 18 is a perspective view of the device of FIG. 17 with the handle 171 detached, showing attachment to the handle post 147.

Figure 19:
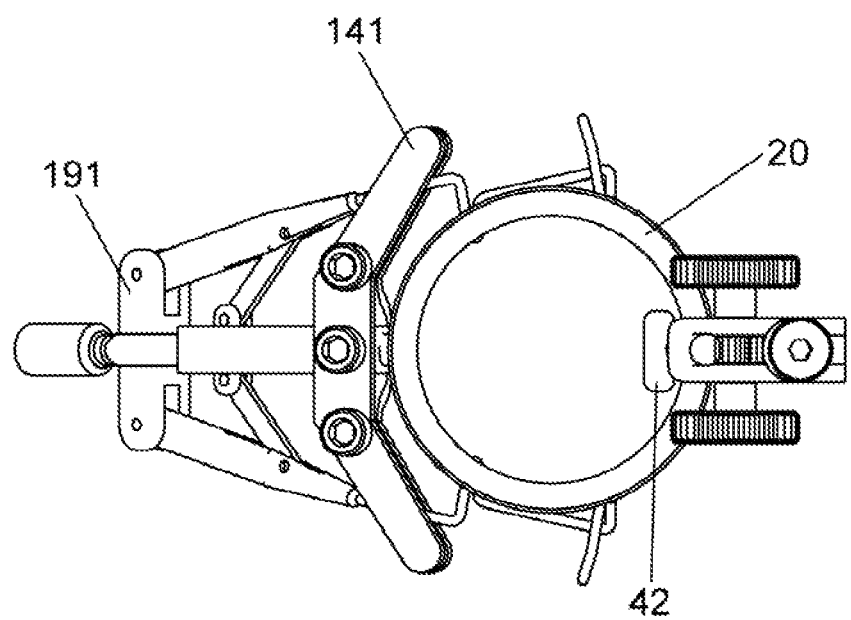
FIG. 19 is a top plan view of the device of FIG. 17.

FIG. 19 is a top plan view of the device of FIG. 17 showing an eyelid speculum 191 with the scleral depression mechanical assist device attached by way of the speculum retainer 141. Also shown in this top plan view is the depressing member 42.

Figure 20:
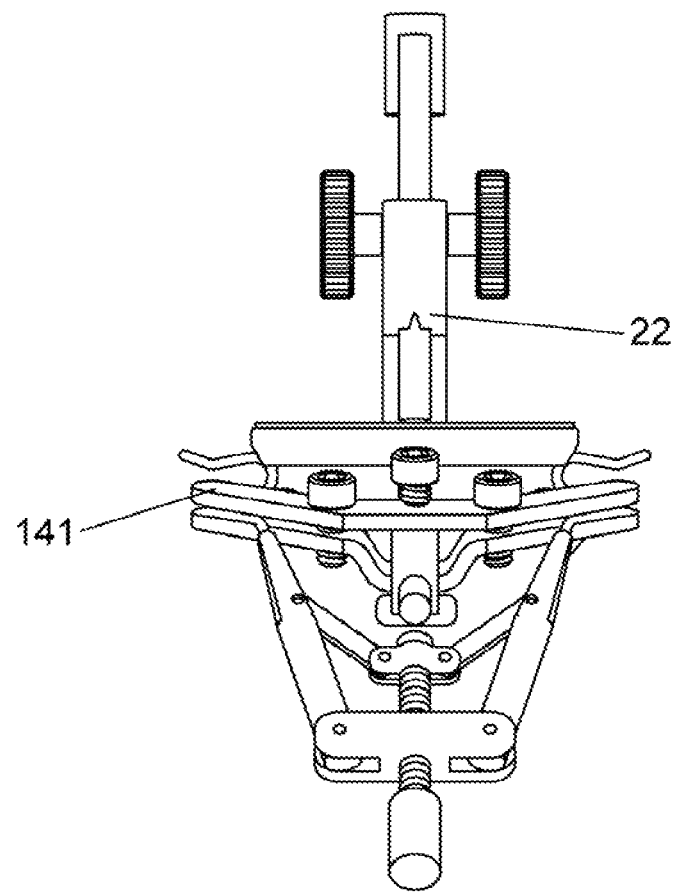
FIG. 20 is a side view of the device of FIG. 17.
Figure 21:
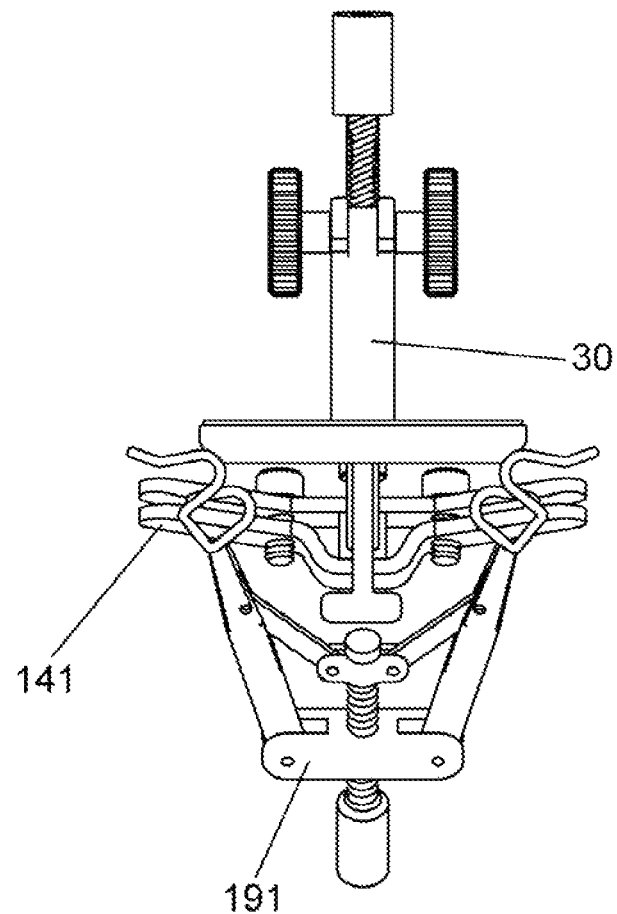
FIG. 21 is an alternate side plan view of the device of FIG. 17.
Figure 22:
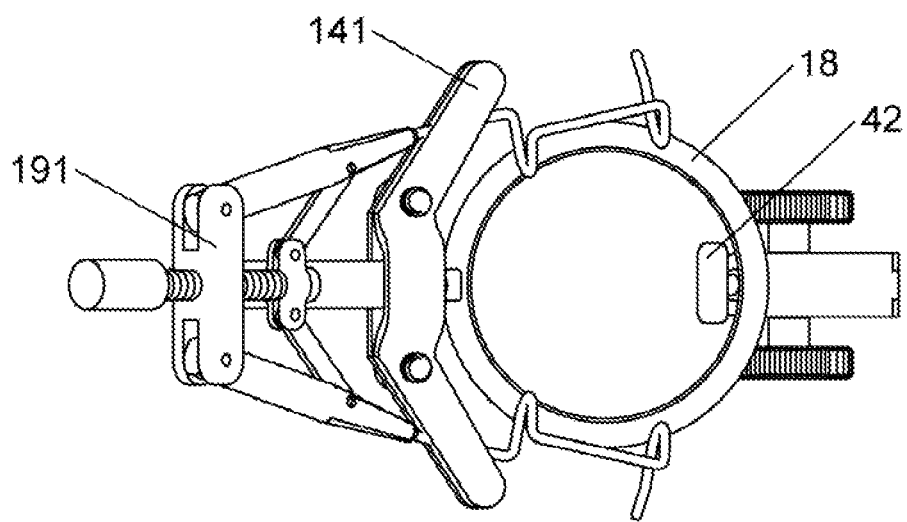
FIG. 22 is a bottom plan view of the device of FIG. 17.
Figure 23:
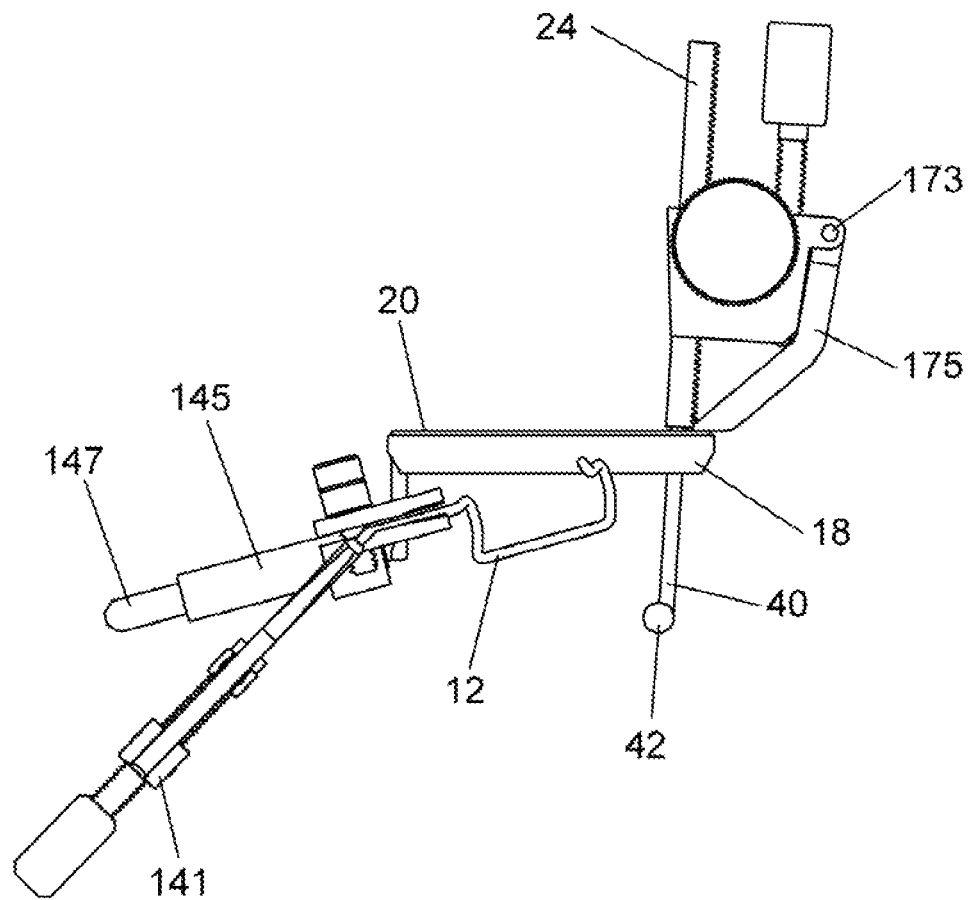
FIG. 23 is a side plan view of the device of FIG. 17.
Figure 24:
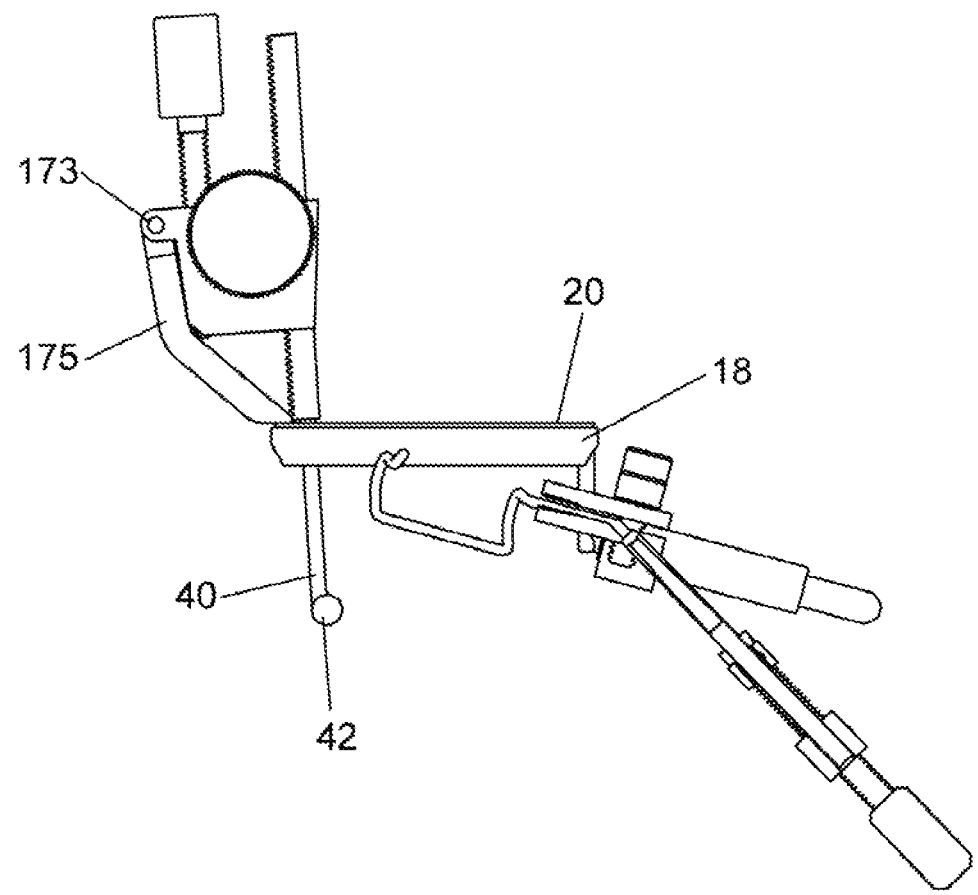
FIG. 24 is an alternate side plan view of the device of FIG. 17.
Figure 25A:
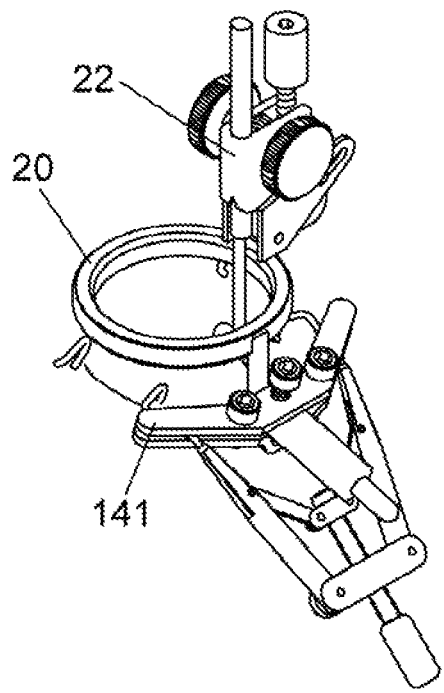
FIGS. 25A-25D sequentially depicts an alternate embodiment of the scleral depression mechanical assist device in circumferential operation.
Figure 25B:
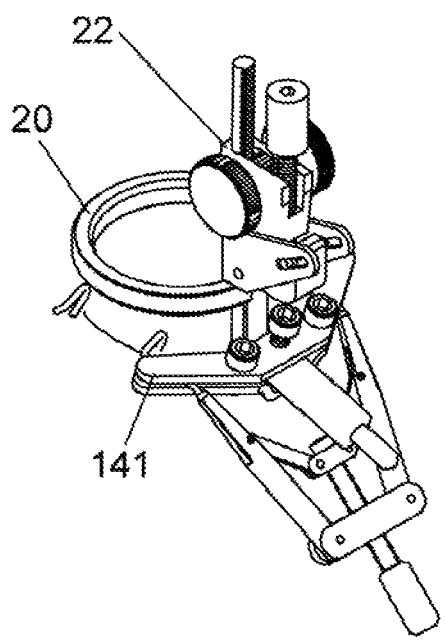
Figure 25C:
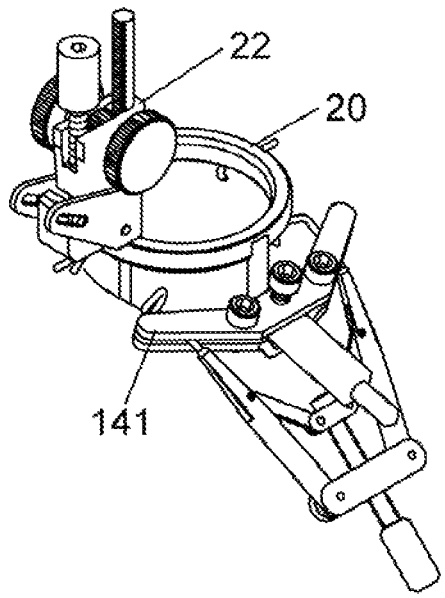
Figure 25D:
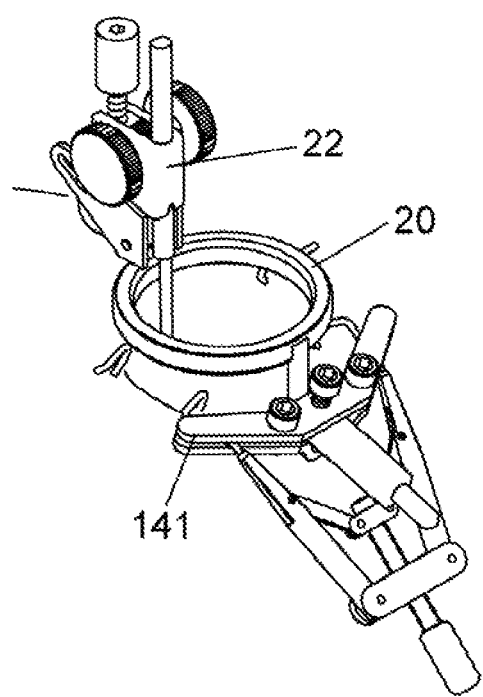

FIG. 20 is a side view of the device of FIG. 17 showing how the speculum retainer 141 attaches the scleral depression mechanical assist device to the eyelid speculum. FIG. 21 is an alternate side plan view of the device of FIG. 17. FIG. 22 is a bottom plan view of the device of FIG. 17. FIG. 23 is a side plan view of the device of FIG. 17. FIG. 24 is an alternate side plan view of the device of FIG. 17.

As has been previously described herein, the scleral depression mechanical assist device attaches to an eyelid speculum and can be adjusted such that a depressing member 42 engages with the eye to form a temporary concave deformation of the eye. The variable vertical displacement apparatus 22 is attached to a top ring 20 that in turn circumferentially rotates with the top ring 20 while the bottom ring 18 remains fixed in position with the eyelid speculum.

FIGS. 25A-25D depict the scleral depression mechanical assist device in circumferential operation where each of FIGS. 25A-25D depict the variable vertical displacement apparatus 22 sequentially and circumferentially moving in 90 degree increments. While FIGS. 25A-25D depict four positions of the device, it should be noted that the variable vertical displacement apparatus 22 is free to move in any position around the entire 360 degree circumference of the ring structure depicted.

Figure 26:
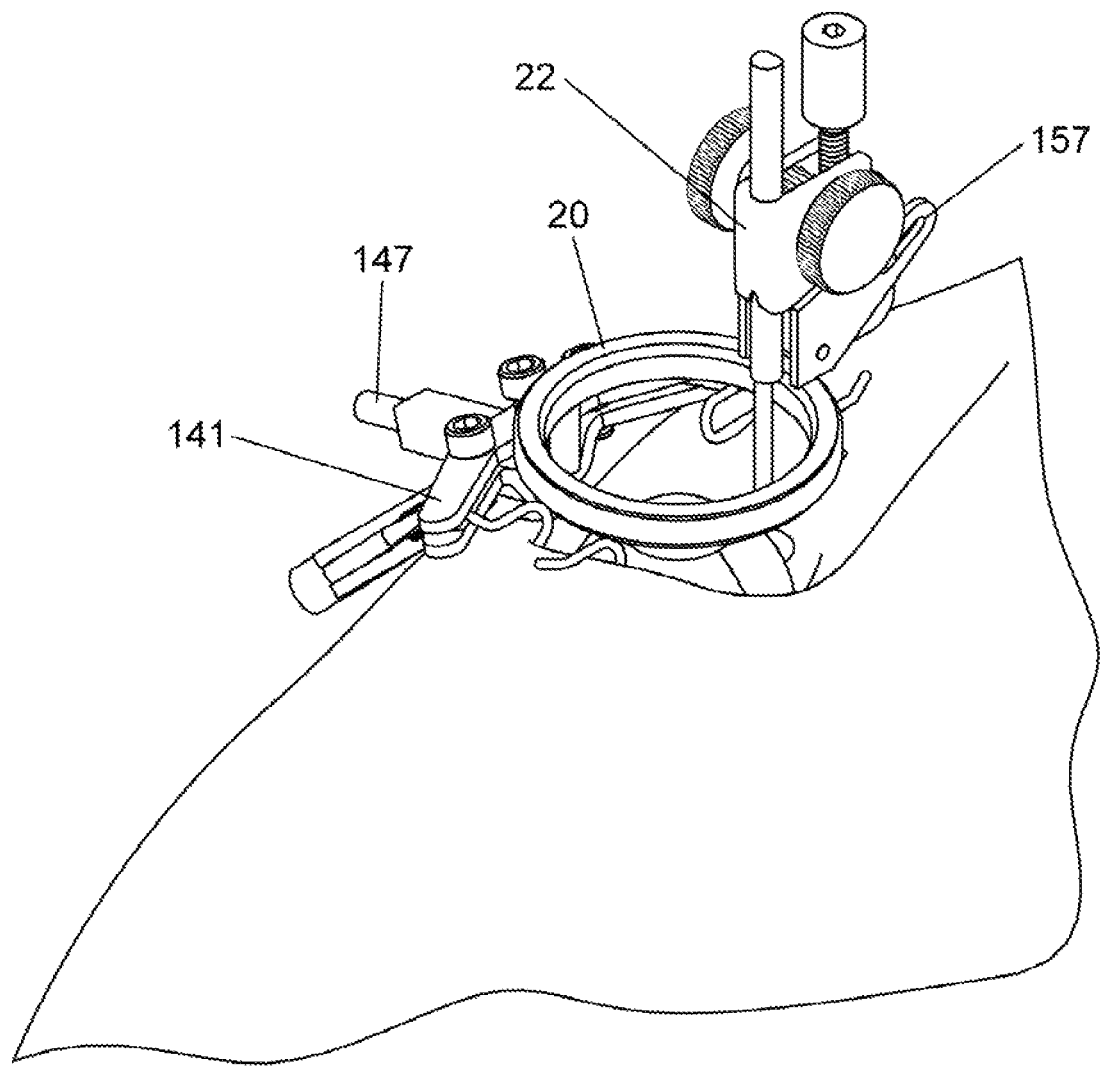
FIG. 26 is a perspective view of the alternate embodiment in use.

FIG. 26 is a perspective view of the scleral depression mechanical assist device in use with a patient. The handle is detached in FIG. 26 with a handle post 147 depicted. It should be noted that a practitioner may choose to omit the handle and operate the device generally as depicted in FIG. 26.

Figure 27:
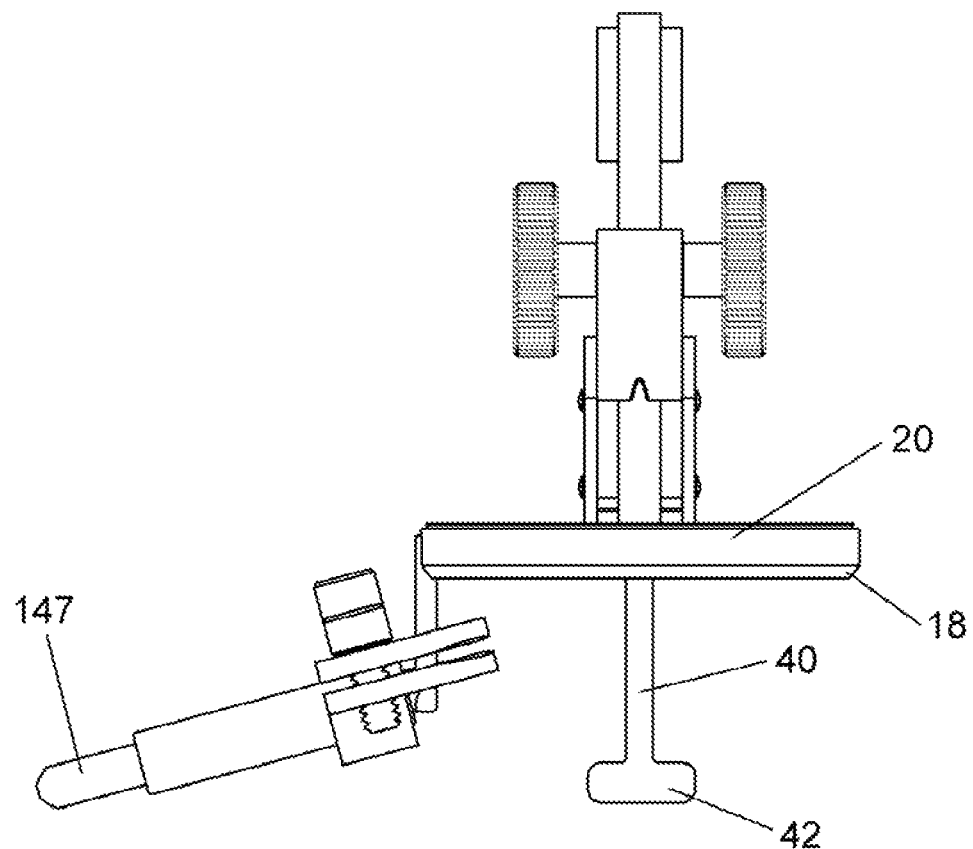
FIG. 27 is a side plan view of the alternate embodiment of FIG. 26.
Figure 28:
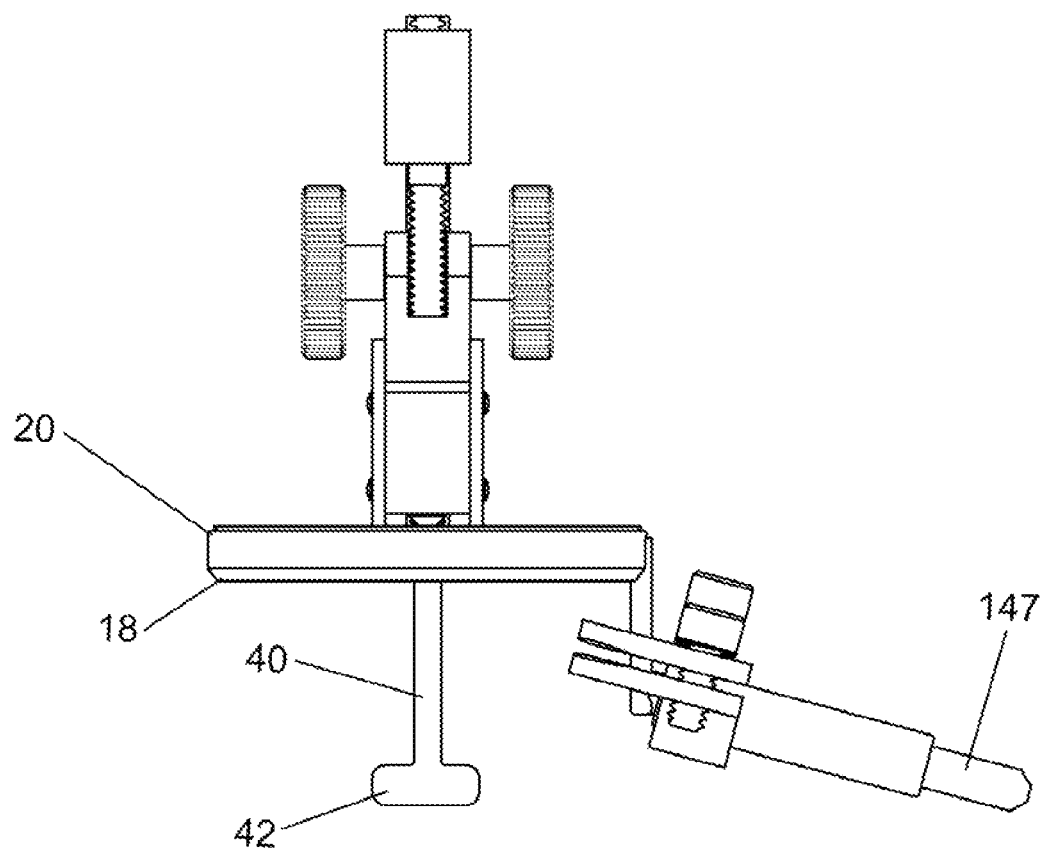
FIG. 28 is a rotated side plan view of the alternate embodiment of FIG. 26.
Figure 29:
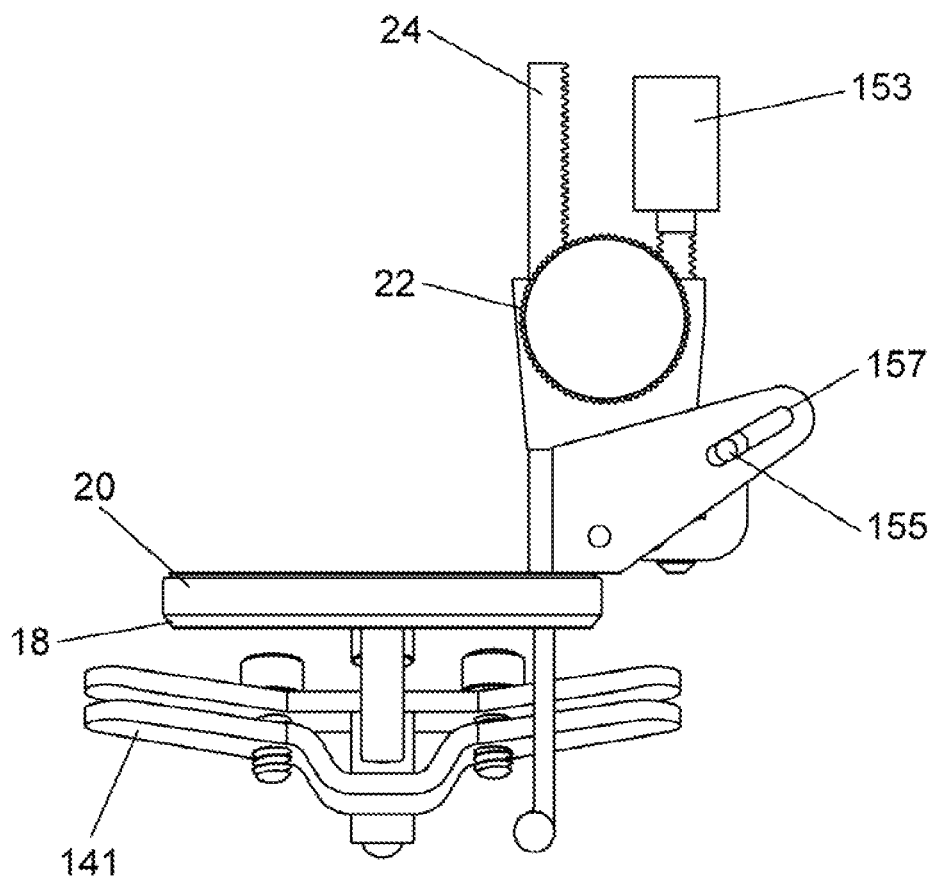
FIG. 29 is a further rotated side plan view of the alternate embodiment of FIG. 26.
Figure 30:
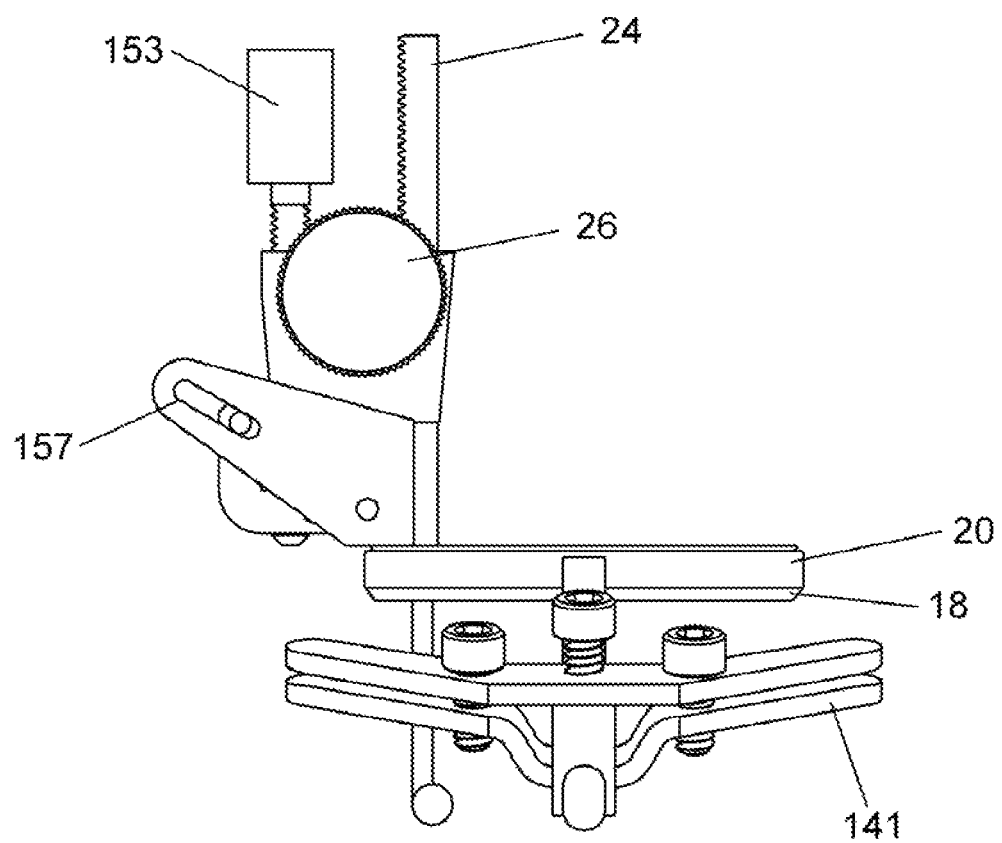
FIG. 30 is another rotated side plan view of the alternate embodiment of FIG. 26.
Figure 31A:
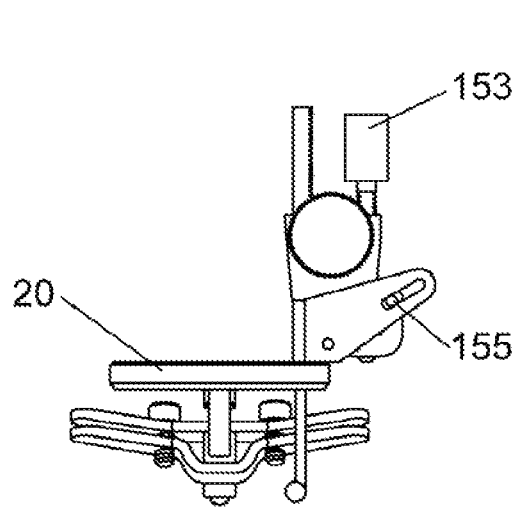
FIGS. 31A-31D depict the angular displacement of the rod and depressing member of the device of the present invention.
Figure 31B:
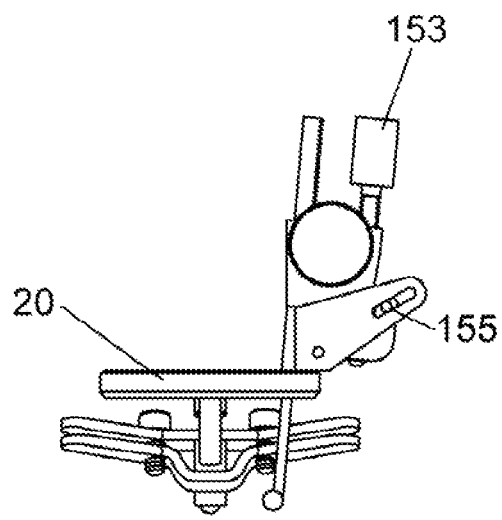
Figure 31C:
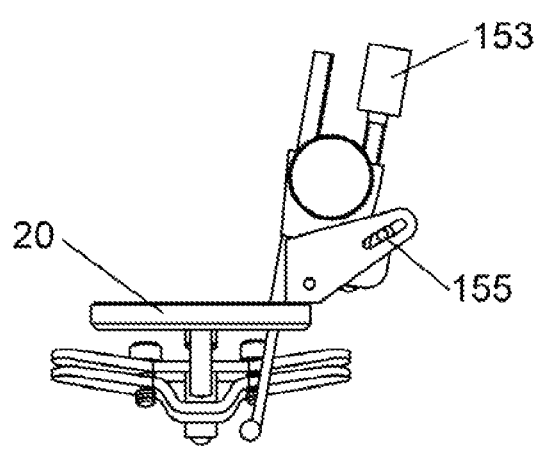
Figure 31D:
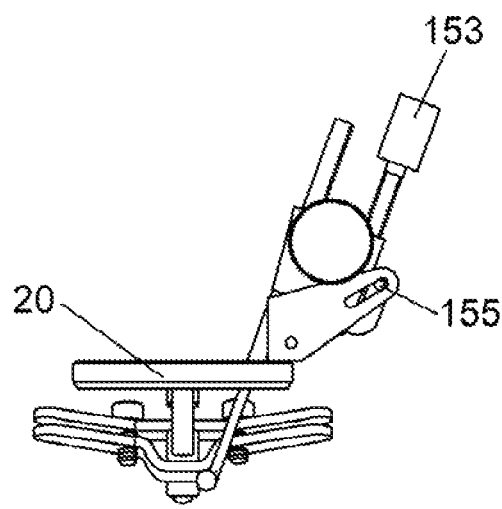

FIG. 27 is a side plan view of the scleral depression mechanical assist device of FIG. 26, and FIG. 28 is a rotated side plan view of the scleral depression mechanical assist device. FIG. 29 is a further rotated side plan view of the device of FIG. 26, and FIG. 30 is another rotated side plan view of the device of FIG. 26.

As described previously, the rod 40 and depressing member 42 can move or otherwise be adjusted in, for example, an arc with both a horizontal and a vertical component by way of rotation or movement of a horizontal adjustment post 153. FIGS. 31A-31D depict this horizontal or angular displacement of the rod and depressing member of the device of the present invention. As the horizontal adjustment post 153 is displaced vertically through rotation, the variable vertical displacement apparatus 22 moves pivotally, in turn moving the rod and depressing member horizontally.

Figure 32:
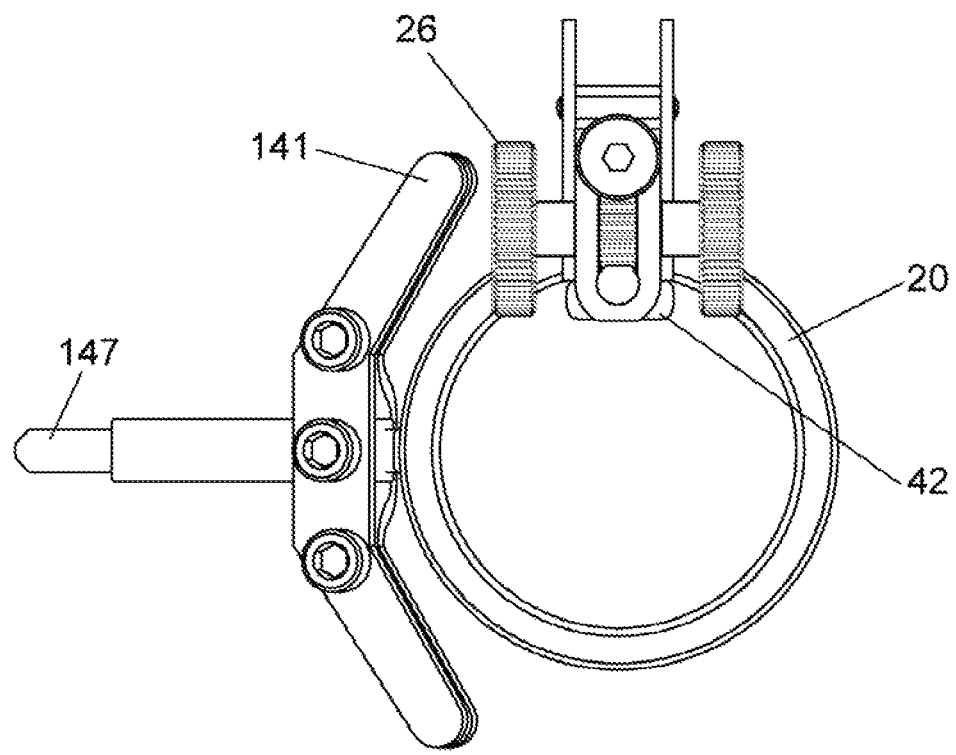
FIG. 32 depicts a top plan view of the alternate embodiment of FIG. 26.
Figure 33:
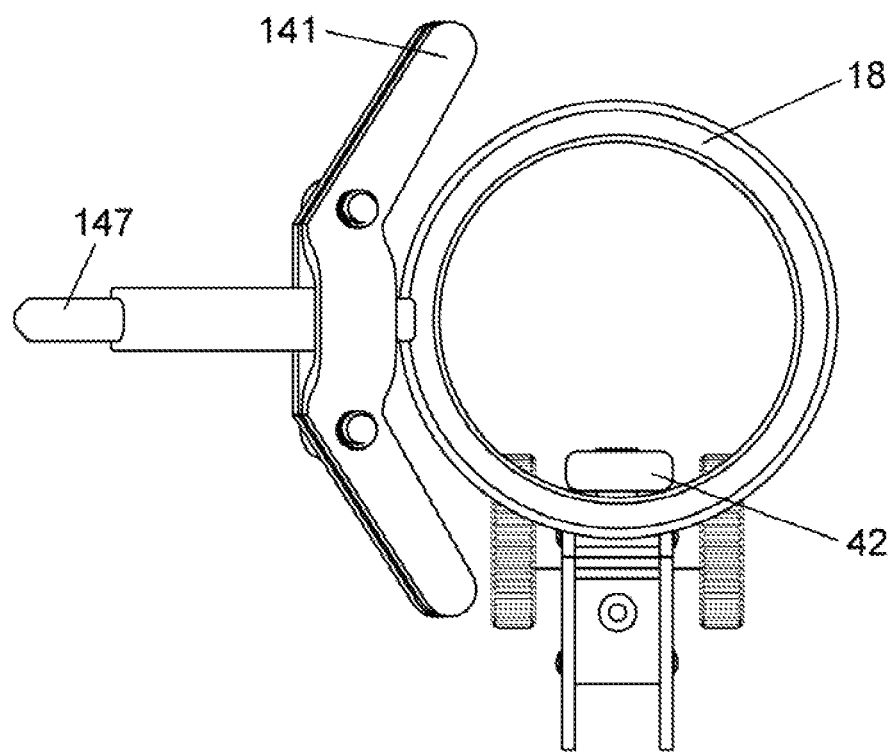
FIG. 33 depicts a bottom plan view of the alternate embodiment of FIG. 26.

FIG. 32 depicts a top plan view of the device of FIG. 26 where the eyelid speculum retainer 141 can be clearly seen attached to the device. No eyelid speculum is present in FIG. 26. FIG. 33 depicts a bottom plan view of the device of FIG. 26.

Figure 34:
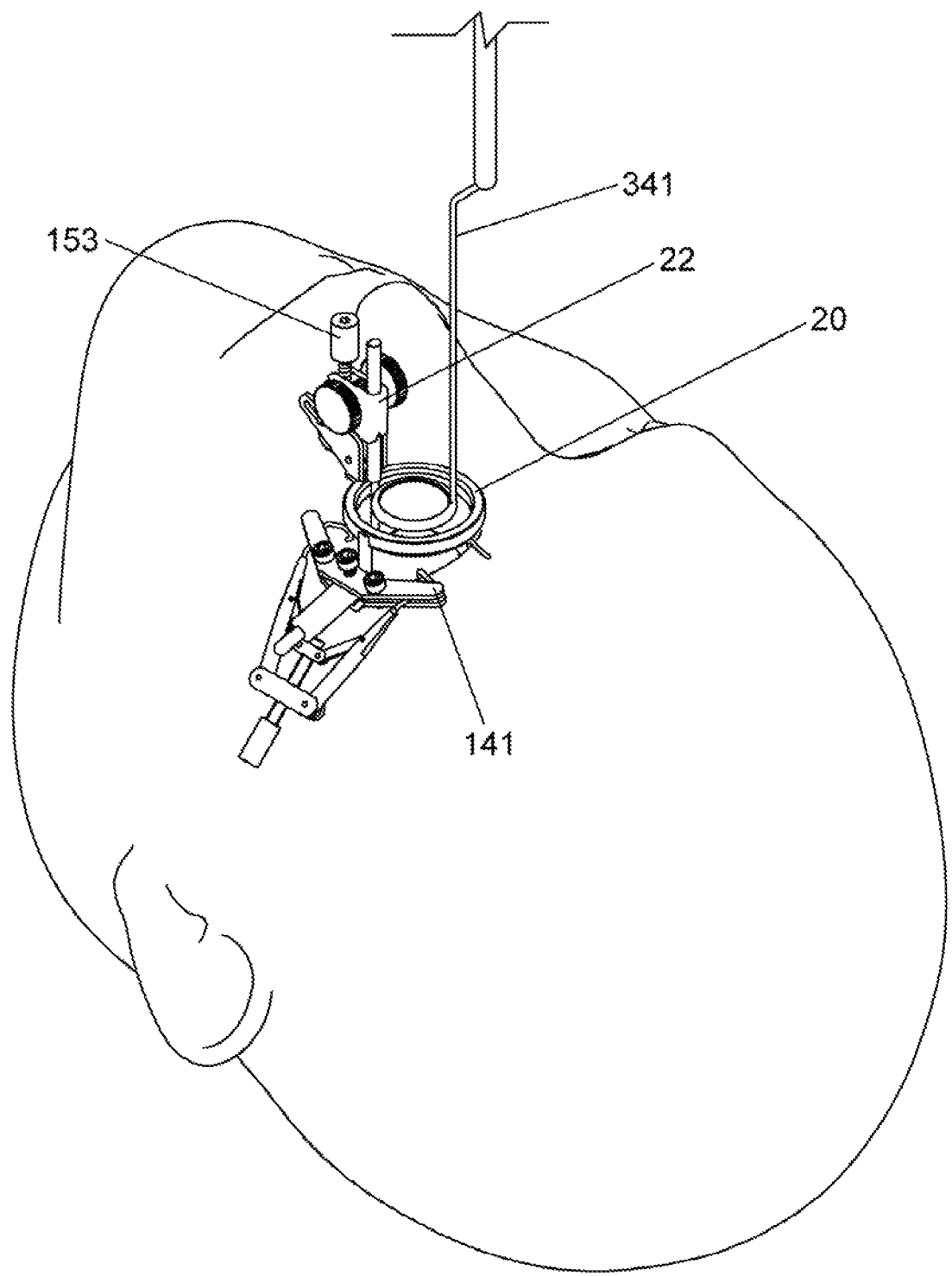
FIG. 34 depicts the scleral depression mechanical assist device in use with a lens and microscope system.

One of the important benefits of the scleral depression mechanical assist device of the present invention is the ability to use various lenses, microscope systems, diagnostic equipment, surgical equipment, and the like due to the ring-like form of the device. For example, FIG. 34 depicts the scleral depression mechanical assist device in use with a lens and microscope system where a lens support 341 can be seen with a lens on the distal end of the support, and close to the eye. Such a lens support 341 may be attached to a microscope system, for example. Other lenses, including surface contact lenses, may also be readily used with the device of the present invention.

Figure 35A:
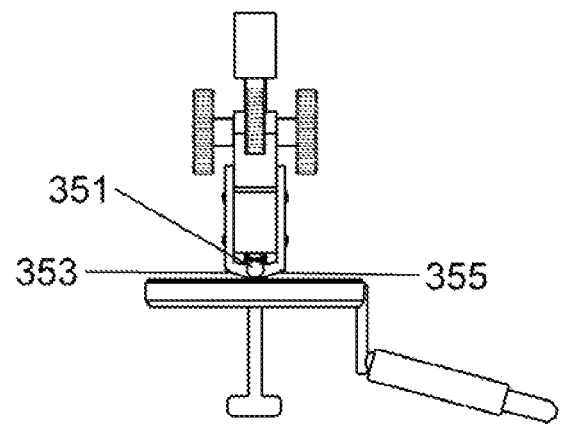
FIGS. 35A-35C depict the axis of rotation of a further embodiment of the scleral depression mechanical assist device.
Figures 35B, 35C:
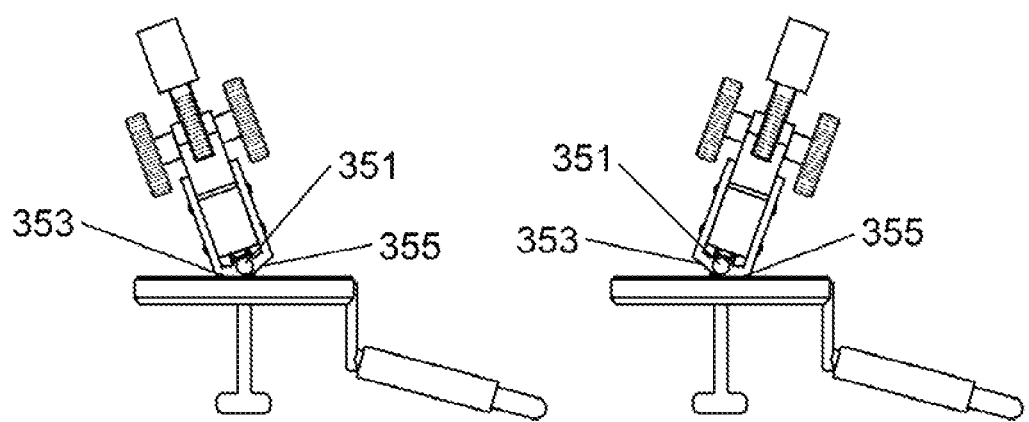

Adjustability of the scleral depression mechanical assist device is important for a variety of procedures. As such, some embodiments may include a further axis of rotation where a pivot 351 which includes a pin or hinge like structure can be seen in FIGS. 35A-35C. The pivot 351 allows the variable vertical displacement apparatus to move side to side. It is important that this side to side movement is limited so as not to over travel and harm the patient. A first angle stop 353 and a second angle stop 355 can be seen in 35A. 351 and 35C where the angle stop prevents excessive side to side travel, thus protecting the patient.

Figure 36:
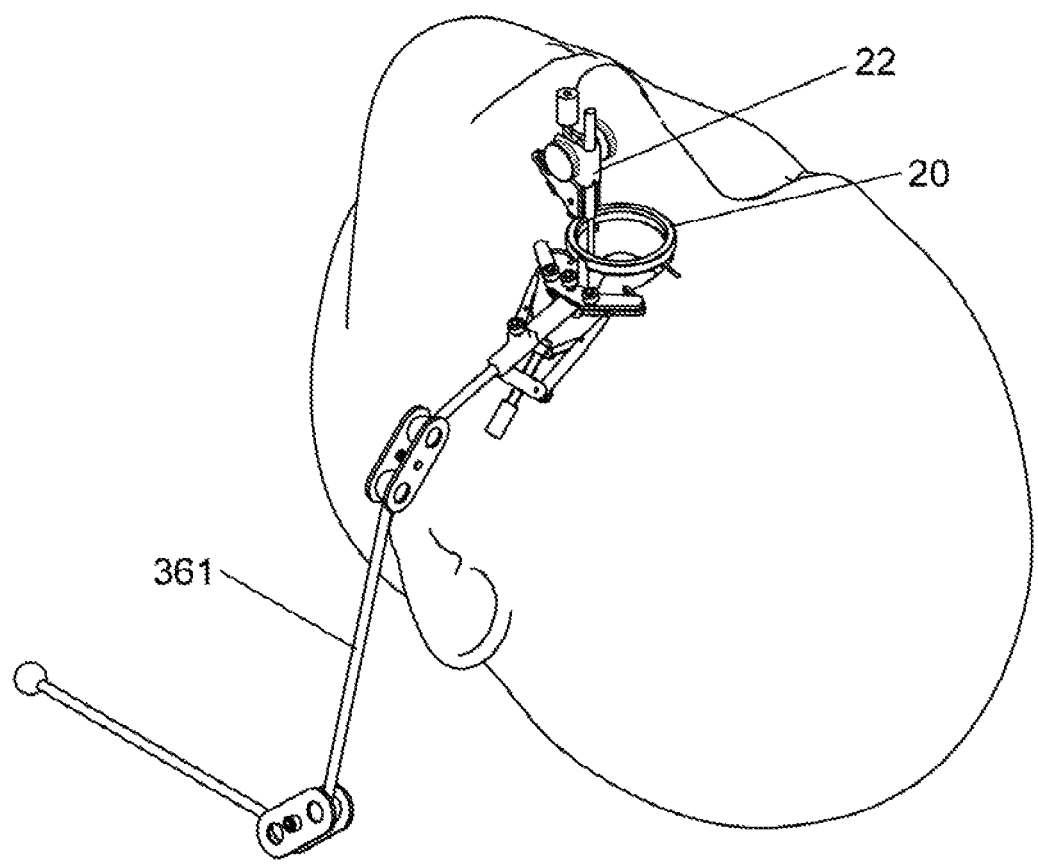
FIG. 36 depicts an assistant handle system with the scleral depression mechanical assist device.

While a simple handle has been previously described herein, an assistant handle system can be seen in FIG. 36 were the handle is articulated with several joints to provide additional degrees of freedom for the medical practitioner.

Figure 37:
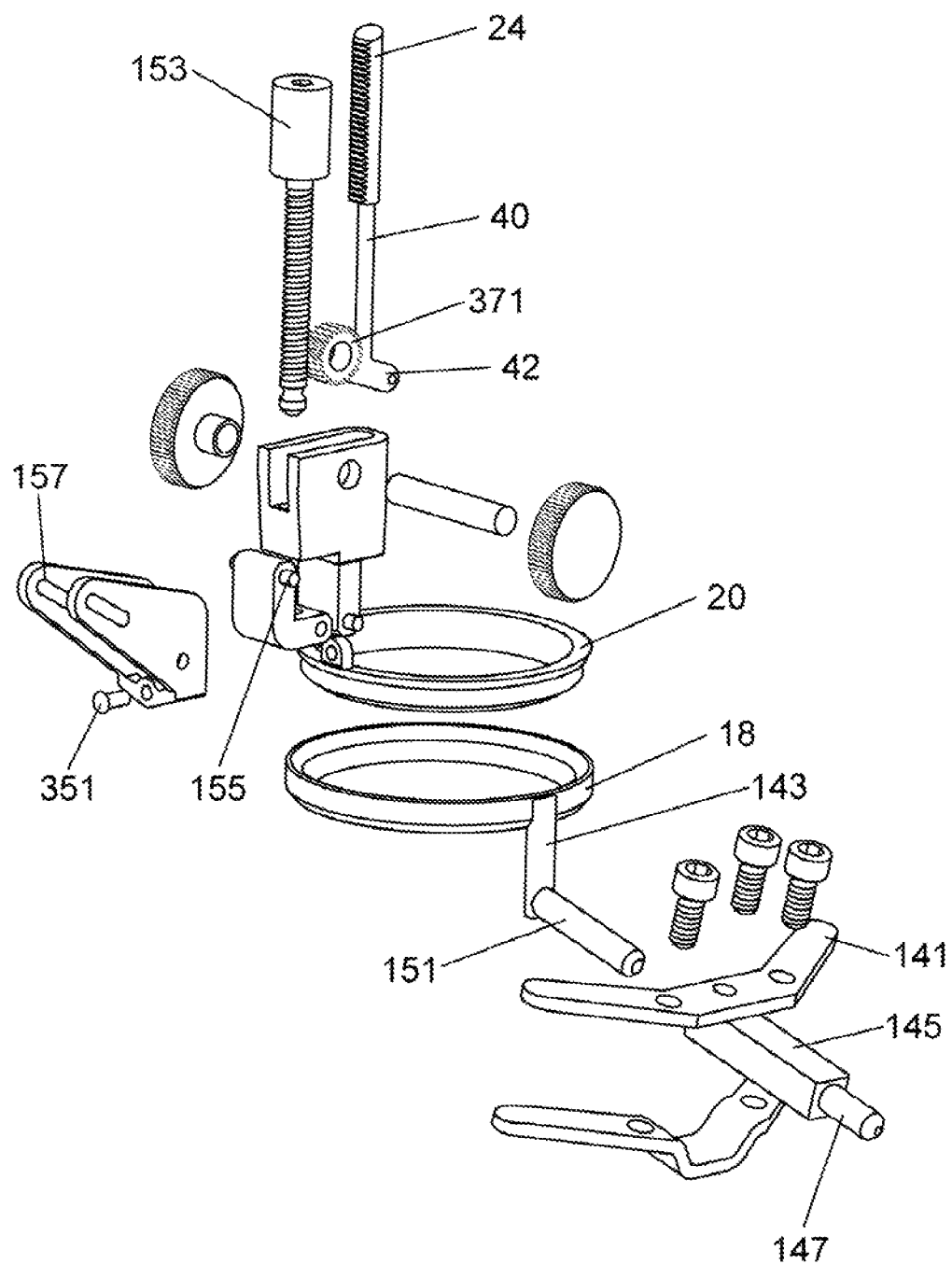
FIG. 37 depicts an exploded view of the scleral depression mechanical assist device.

Lastly. FIG. 37 depicts an exploded view of the scleral depression mechanical assist device. The way in which the various components interconnect and mechanically cooperate with each other, while generally evident with the disclosure and related figures provided heretofore, may become even more clear with the exploded view of one exemplary embodiment of the scleral depression mechanical assist device seen in FIG. 37. In particular, while previously described, gear 371 was not visible in previous figures, but can be clearly seen in FIG. 37. The gear 371 is retained by a pin or axle and engages with the rack gear 24, transferring vertical displacement to the rack gear 24 and connected rod 40 and depressing member 42. In some embodiments, a frictional device (not shown in FIG. 37) may be employed to prevent the rod 40 and depressing member 42 from traveling vertically downward.

While various embodiments, accessories and attachments have been described herein, the scleral depression mechanical assist device comprises a ring for attachment to a device such as an eyelid speculum, a variable vertical displacement apparatus rotationally coupled to the ring, a rod having an adjustment end and a surgical end, and a depressing member attached to the surgical end of the rod, where the adjustment end of the rod is adjustably coupled to the variable vertical displacement apparatus.

To use the scleral depression mechanical assist device, the speculum retainer is attached to an eyelid speculum which is in turn placed on a patient undergoing a medical procedure. The rod and depressing member are adjusted by way of mechanisms previously described herein such that the depressing member presses against the eye, creating a concave form in the eye. The variable vertical displacement apparatus that has the rod and depressing member attached is free to rotate circumferentially about the ring of the device, where the position of the rod and depressing member can be adjusted.

What is claimed is:

1. A device for mechanically assisting with scleral depression, the device comprising:
    a top ring rotationally disposed with a bottom ring;
    a locking member attached to the bottom ring for attachment to an eyelid speculum;
    an upright frame member attached to the top ring;
    a rod having an adjustment end and a surgical end;
    a variable vertical displacement apparatus mechanically coupled to both the upright frame member and the rod;
    the variable vertical displacement apparatus configured to provide vertical displacement to the rod;
    a depressing member attached to the surgical end of the rod; and
    an adjusting member for providing horizontal displacement to the rod and depressing member.

2. The device of claim 1, wherein the variable vertical displacement apparatus is pivotally attached to the upright frame member along a first axis.

3. The device of claim 2, wherein the variable vertical displacement apparatus is pivotally attached to the upright frame member along both the first axis and a second axis.

4. The device of claim 1, wherein the variable vertical displacement apparatus is moveably attached to the upright frame member.

5. The device of claim 1, wherein the variable vertical displacement apparatus comprises a rack gear mechanically coupled to the rod and a gear for engagement with the rack gear to provide vertical displacement to the rod.

6. The device of claim 5, further comprising a knob attached to the gear for tactile rotation of the gear and adjustment of the vertical displacement of the rod.

7. The device of claim 1, further comprising a surgical handle.

8. The device of claim 7, wherein the surgical handle is reticulated.

9. The device of claim 1, further comprising a nose bridge.

10. The device of claim 1, further comprising a stabilizer strut.

11. A device for mechanically assisting with scleral depression, the device comprising:
    a top ring rotationally disposed with a bottom ring;
    an eyelid speculum attached to the bottom ring;
    an upright frame member attached to the top ring;
    a rod having an adjustment end and a surgical end;
    a variable vertical displacement apparatus mechanically coupled to both the upright frame member and the rod;
    the variable vertical displacement apparatus configured to provide vertical displacement to the rod;
    a depressing member attached to the surgical end of the rod; and
    an adjusting member for providing horizontal displacement to the rod and depressing member.

12. The device of claim 11, wherein the variable vertical displacement apparatus is pivotally attached to the upright frame member along a first axis.

13. The device of claim 11, wherein the variable vertical displacement apparatus is pivotally attached to the upright frame member along both the first axis and a second axis.

14. The device of claim 11, wherein the variable vertical displacement apparatus is moveably attached to the upright frame member.

15. The device of claim 11, wherein the variable vertical displacement apparatus comprises a rack gear mechanically coupled to the rod and a gear for engagement with the rack gear to provide vertical displacement to the rod.

16. The device of claim 15, further comprising a knob attached to the gear for tactile rotation of the gear and adjustment of the vertical displacement of the rod.

17. The device of claim 11, further comprising a surgical handle.

18. The device of claim 11, further comprising a nose bridge.

19. The device of claim 11, further comprising a stabilizer strut.

20. The device of claim 11, further comprising a lens.

21. A device for mechanically assisting with scleral depression, the device comprising:
- a top ring rotationally disposed with a bottom ring;
- a locking member attached to the bottom ring for attachment to an eyelid speculum;
- an upright frame member attached to the top ring;
- a rod having an adjustment end and a surgical end;
- a variable vertical displacement apparatus mechanically coupled to both the upright frame member and the rod;
- the variable vertical displacement apparatus configured to provide vertical displacement to the rod;
- a depressing member attached to the surgical end of the rod;
- an adjusting member for providing horizontal displacement to the rod and depressing member; and
- a lens.

* * * * *